(12) United States Patent
Zhu et al.

(10) Patent No.: US 9,793,485 B2
(45) Date of Patent: Oct. 17, 2017

(54) BENZOCYCLOBUTENES DERIVED COMPOSITIONS, AND ELECTRONIC DEVICES CONTAINING THE SAME

(71) Applicants: Dow Global Technologies LLC, Midland, MI (US); Rohm and Haas Electronic Materials LLC, Marlborough, MA (US)

(72) Inventors: Minrong Zhu, Shanghai (CN); Jichang Feng, Shanghai (CN); Shaoguang Feng, Shanghai (CN); Chun Liu, Midland, MI (US); Nolan T. McDougal, Houston, TX (US); David D. Devore, Midland, MI (US); Peter Trefonas, III, Medway, MA (US); Liam P. Spencer, Manvel, TX (US)

(73) Assignees: Dow Global Technologies LLC, Midland, MI (US); Rohm and Haas Electronic Materials LLC, Marlbourough, MA (US)

( * ) Notice: Subject to any disclaimer, the term of this patent is extended or adjusted under 35 U.S.C. 154(b) by 0 days.

(21) Appl. No.: 15/328,330

(22) PCT Filed: Aug. 19, 2015

(86) PCT No.: PCT/US2015/045915
§ 371 (c)(1),
(2) Date: Jan. 23, 2017

(87) PCT Pub. No.: WO2016/028902
PCT Pub. Date: Feb. 25, 2016

(65) Prior Publication Data
US 2017/0229656 A1  Aug. 10, 2017

(30) Foreign Application Priority Data
Aug. 21, 2014  (WO) ................ PCT/CN2014/084915

(51) Int. Cl.
| | | |
|---|---|---|
| C07D 209/86 | (2006.01) | |
| H01L 51/00 | (2006.01) | |
| C08G 61/12 | (2006.01) | |
| H01L 51/50 | (2006.01) | |

(52) U.S. Cl.
CPC ........ *H01L 51/0039* (2013.01); *C07D 209/86* (2013.01); *C08G 61/124* (2013.01); *H01L 51/0043* (2013.01); *C08G 2261/124* (2013.01); *C08G 2261/18* (2013.01); *C08G 2261/228* (2013.01); *C08G 2261/314* (2013.01); *C08G 2261/3142* (2013.01); *C08G 2261/3162* (2013.01); *C08G 2261/3241* (2013.01);
(Continued)

(58) Field of Classification Search
CPC ............ H01L 51/0039; H01L 51/0043; H01L 51/5056; C07D 209/86; C08G 61/124; C08G 2261/124; C08G 2261/18; C08G 2261/228; C08G 2261/314; C08G 2261/3142; C08G 2261/3162; C08G 2261/3241; C08G 2261/512; C08G 2261/95
USPC ........................................ 548/440
See application file for complete search history.

(56) References Cited

U.S. PATENT DOCUMENTS

| | | |
|---|---|---|
| 7,893,160 B2 | 2/2011 | Inbasekaran et al. |
| 2004/0004433 A1 | 1/2004 | Lamansky et al. |
| 2007/0096082 A1 | 5/2007 | Gaynor et al. |

(Continued)

FOREIGN PATENT DOCUMENTS

| | | |
|---|---|---|
| CN | 102329411 A | 1/2012 |
| EP | 2421064 A2 | 2/2012 |

(Continued)

OTHER PUBLICATIONS

Dobish, J.N.; Hamilton, S.K.; Harth, E. *Polymer Chemistry* 2012, 3, 857-860.
Ma Biwu, et al. New Thermally Cross-Linkable Polymer and Its application as a hole-transporting layer for solution processed Multilayer Organic Light Emitting Diodes Chem. Mater. Aug. 25, 2007, No. 19, vol. 19 pp. 4827-4832.
(Continued)

*Primary Examiner* — Kristin Vajda
(74) *Attorney, Agent, or Firm* — Andrew E.C. Merriam

(57) ABSTRACT

The invention provides compositions comprising crosslinkable BCB-functionalized materials for use in OLEDs applications. The inventive compositions can be used to form hole-transporting materials for use in electroluminescent devices. In particular, the invention provides a composition comprising at least one compound selected from Structure A, as described herein.

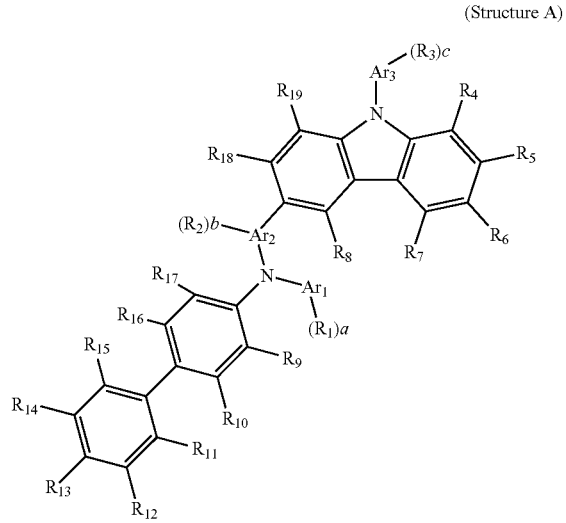

(Structure A)

15 Claims, No Drawings

(52) U.S. Cl.
CPC ... *C08G 2261/512* (2013.01); *C08G 2261/95* (2013.01); *H01L 51/5056* (2013.01)

(56) References Cited

U.S. PATENT DOCUMENTS

| | | |
|---|---|---|
| 2007/0181874 A1 | 8/2007 | Prakash et al. |
| 2008/0309229 A1 | 12/2008 | Steudel et al. |
| 2008/0315757 A1 | 12/2008 | McKiernan et al. |
| 2010/0133566 A1 | 6/2010 | Towns et al. |
| 2011/0042661 A1 | 2/2011 | Endo et al. |
| 2011/0065222 A1 | 3/2011 | Meyer et al. |
| 2011/0089411 A1 | 4/2011 | Xia et al. |
| 2011/0095278 A1 | 4/2011 | Sugita et al. |
| 2011/0198573 A1 | 8/2011 | Iida et al. |
| 2012/0001127 A1 | 1/2012 | Brown et al. |
| 2012/0003790 A1 | 1/2012 | Brown et al. |
| 2012/0037894 A1 | 2/2012 | Okabe |

FOREIGN PATENT DOCUMENTS

| | | |
|---|---|---|
| JP | 2009170764 A2 | 7/2009 |
| JP | 2010062120 A | 3/2010 |
| WO | WO-2007/052027 A1 | 5/2007 |
| WO | WO-2012/052704 A2 | 4/2012 |
| WO | WO-2012/175975 A2 | 12/2012 |
| WO | WO-2013/007966 A1 | 1/2013 |
| WO | WO-2013/060418 A1 | 5/2013 |
| WO | WO-2015/030169 A1 | 3/2015 |
| WO | WO-2016/028906 A1 | 2/2016 |

OTHER PUBLICATIONS

PCT/CN2014/084915 Search Report and Written Opinion dated May 22, 2015.

PCT/US2015/045915 Search Report and Written Opinion dated Nov. 4, 2015.

PCT/US2015/045915 International Preliminary Report on Patentability dated Mar. 2, 2017.

BENZOCYCLOBUTENES DERIVED COMPOSITIONS, AND ELECTRONIC DEVICES CONTAINING THE SAME

REFERENCE TO RELATED APPLICATIONS

The present application claims priority to International Application No. PCT/CN14/084915, filed Aug. 21, 2014, and incorporated herein by reference.

BACKGROUND

Organic light-emitting diodes (OLEDs) have attracted considerable interest for the potential applications, as the next generation flat-panel displays and solid-state lighting sources. OLEDs are double charge injection devices, which require the simultaneous supply of both holes and electrons to the emissive layer. To realize facile and balanced charge transport, most highly efficient OLEDs tend to have multilayer device configurations, a hole transport layer (HTL), an electron transport layer (ETL) and an emissive layer (EML), some also have a hole-injection and an electron injection layer. The charge injection/transport layers are used to inject and transport holes and electrons to the EML, where the charges recombine and form the excitons. There is continuous need to develop new charge transport materials to improve device performance and lifetime.

In the case of the HTL layer, the process by which the layer is deposited is critical for its end-use application. Methods for depositing the HTL layer in small display applications involve evaporation of a small organic compound with a fine metal mask to direct the deposition. Solution processes, such as spin-coating, inkjet printing and roll-to-roll fabrication, offer an attractive alternative approach, in terms of their low-cost and large-area manufacturability, which is more amenable to commercial interests. With these findings in mind, new compositions and processes are still needed to deposit HTLs, and which satisfy these challenges, and which can be directly applied to large display applications.

Although some polymeric materials can be fabricated by a solution process, their batch-to-batch variations in solubility, molecular weight, and purity, can result in different processing properties and device performance. Since higher molecular precision of small-molecule materials can overcome the abovementioned discrepancies, the development of solution-processable, small-molecule materials, suitable for OLEDs, is highly desirable to realize this goal. One approach that appears promising is a solution process, which involves the deposition of a small molecule, followed by crosslinking or polymerization chemistry. There have been extensive efforts in this area along these lines; however these chemistries have their own shortcomings. In particular, the current technology can hardly produce an insoluble HTL film, with few to no reactive end groups, at desirable process conditions.

The benzocyclobutene (BCB) group is an example of a moiety that undergoes a thermally activated dimerization, typically at 200° C. or above, in this case, forming a dibenzocyclooctadiene ring, which is formed by scission of one of the cyclobutene C—C bonds, followed by an irreversible cycloaddition. It is been documented in the open literature that the substitution of oxygen-based donors, at the cyclobutene ring above, has a dramatic effect on the ring-opening temperature of the BCB (Dobish, J. N.; Hamilton, S. K.; Harth, E. *Polymer Chemistry* 2012, 3, 857-860); this phenomenon has yet to be utilized for OLEDs applications.

Benzocyclobutene (BCB) chemistries and their use in OLEDs are described in the following: US20040004433, US20080315757, US20080309229, US20100133566, US20110095278, US20110065222, US20110198573, US20110042661, JP2010062120, U.S. Pat. No. 7,893,160, US20110089411, US20070181874, US20070096082, CN102329411, US20120003790, WO2012052704, WO2012175975, WO2013007966, International Application PCT/CN14/084918 (filed Aug. 21, 2014), U.S. Prov. 62/039,935 (filed Aug. 21, 2014).

However, there remains a need for new compositions for improved hole-transporting materials, and for improved processing of the same. These needs have been met by the following invention.

SUMMARY OF INVENTION

The invention provides a composition comprising at least one compound selected from Structure A:

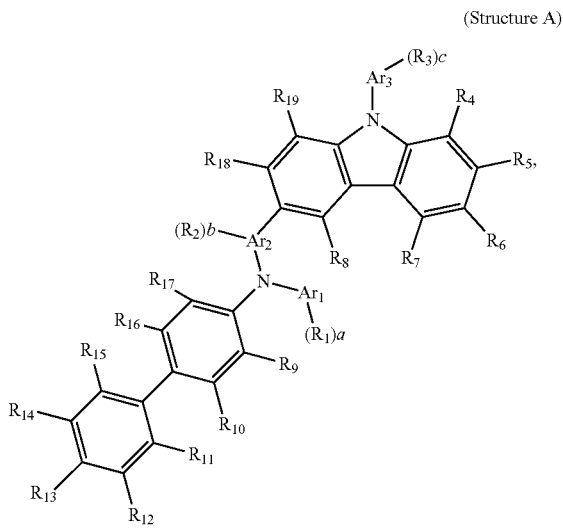

(Structure A)

wherein groups $R_4$ to $R_{19}$ are each, independently, selected from hydrogen, a hydrocarbon, a substituted hydrocarbon, a halogen, a cyano, a nitro, an alkoxy, or a hydroxyl;

$Ar_1$ is selected from a substituted aryl, an unsubstituted aryl, a substituted heteroaryl, or an unsubstituted heteroaryl;

$(R_1)a$ is selected from hydrogen, a hydrocarbon, a substituted hydrocarbon, a halogen, a cyano, a nitro, an alkoxy, or a hydroxyl;

$Ar_2$ is selected from a substituted aryl, an unsubstituted aryl, a substituted heteroaryl, or an unsubstituted heteroaryl;

$(R_2)b$ is selected from hydrogen, a hydrocarbon, a substituted hydrocarbon, a halogen, a cyano, a nitro, an alkoxy, or a hydroxyl;

$Ar_3$ is selected from a substituted aryl, an unsubstituted aryl, a substituted heteroaryl, or an unsubstituted heteroaryl;

$(R_3)c$ is selected from hydrogen, a hydrocarbon, a substituted hydrocarbon, a halogen, a cyano, a nitro, an alkoxy, or a hydroxyl; and with the proviso that at least one of groups $(R_1)a$, $(R_2)b$, $(R_3)c$ or $R_4$ to $R_{19}$ is independently selected from the benzocyclobutene structures of Structure B, Structure C, Structure D, or Structure E, as follows:

(Structure B)

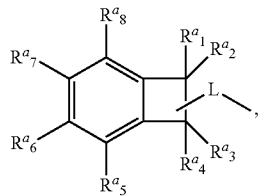

B)

wherein Structure B is connected to Structure A though -L-;
wherein, for Structure B:

1b) one of $R^a_1$, $R^a_2$, $R^a_3$ or $R^a_4$ is -L-; and wherein -L- is selected from the following: —O—; -alkylene-; —O-alkylene-; —O-arylene-; —O-alkylene-arylene-; —O-alkylene-O—; —O-alkylene-O-alkylene-O—; —O-arylene-O—; —O-alkylene-arylene-O—; —O—(CH2CH2-O)n-, wherein n is from 2 to 20; —O-alkylene-O-alkylene-; —O-alkylene-O-arylene-; —O-arylene-O—; —O-arylene-O-alkyene-; —O-arylene-O-arylene-; or a covalent bond linking 'Structure B" to "Structure A"; and 2b) the remaining $R^a_1$, $R^a_2$, $R^a_3$ and $R^a_4$ are each, independently, selected from hydrogen, a hydrocarbon, a substituted hydrocarbon, a halogen, a cyano, a nitro, an alkoxy, or a hydroxyl; and 3b) $R^a_5$, $R^a_6$, $R^a_7$ or $R^a_8$ are each, independently, selected from hydrogen, a hydrocarbon, a substituted hydrocarbon, a halogen, a cyano, a nitro, an alkoxy, or a hydroxyl;

(Structure C)

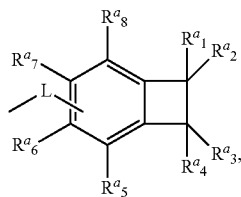

C)

wherein Structure C is connected to Structure A though -L-;
wherein, for Structure C:

1c) one of $R^a_5$, $R^a_6$, $R^a_7$ or $R^a_8$ is -L-; and wherein -L- is selected from the following: —O—; -alkylene-; -arylene-; —O-alkylene-; —O-arylene-; —O-alkylene-arylene-; —O-alkylene-O—; —O-alkylene-O-alkylene-O—; —O-arylene-O—; —O-alkylene-arylene-O—; —O—(CH2CH2-O)n-, wherein n is from 2 to 20; —O-alkylene-O-alkylene-; —O-alkylene-O-arylene-; —O-arylene-O-alkyene-; —O-arylene-O-arylene-; or a covalent bond linking 'Structure C" to "Structure A";

2c) the remaining $R^a_5$, $R^a_6$, $R^a_7$ or $R^a_8$ are each, independently, selected from hydrogen, a hydrocarbon, a substituted hydrocarbon, a halogen, a cyano, a nitro, or a hydroxyl;

3c) $R^a_1$, $R^a_2$, $R^a_3$ and $R^a_4$ are each, independently, selected from hydrogen, a hydrocarbon, a substituted hydrocarbon, a halogen, a cyano, a nitro, an alkoxy, or a hydroxyl;

(Structure D)

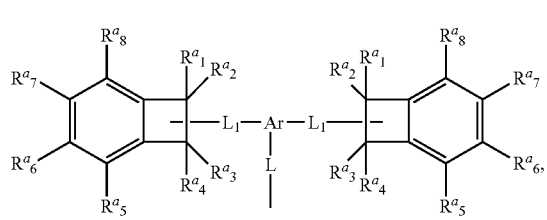

D)

wherein Structure D is connected to Structure A though -L-;
wherein, for Structure D:

1di) for one -$L_1$-, one of $R^a_1$, $R^a_2$, $R^a_3$ or $R^a_4$ of the benzocyclobutene moiety directly bonded to this -$L_1$-, is independently -$L_1$-; and wherein -L1- is selected from the following: —O—; -alkylene-; —O-alkylene-; —O-arylene-; —O-alkylene-arylene-; —O— alkylene-O—; —O-alkylene-O-alkylene-O—; —O-arylene-O—; —O-alkylene-arylene-O—; —O—(CH2CH2-O)n-, wherein n is from 2 to 20; —O-alkylene-O-alkylene-; —O-alkylene-O-arylene-; —O-arylene-O—; —O-arylene-O-alkyene-; —O-arylene-O-arylene-; —O-alkylene-arylene-O—; or a covalent bond linking the 4 carbon ring to Ar;

1dii) for the other -$L_1$-, one of $R^a_1$, $R^a_2$, $R^a_3$ or $R^a_4$ of the other benzocyclo-butene moiety directly bonded to this -$L_1$-, is independently -$L_1$-; and wherein -L1- is selected from the following: —O—; -alkylene-; —O-alkylene-; —O-arylene-; —O-alkylene-arylene-; —O-alkylene-O—; —O-alkylene-O-alkylene-O—; —O-arylene-O—; —O— alkylene-arylene-O—; —O—(CH2CH2-O)n-, wherein n is from 2 to 20; —O-alkylene-O-alkylene-; —O-alkylene-O-arylene-; —O-arylene-O—; —O-arylene-O-alkyene-; —O-arylene-O-arylene-; —O-alkylene-arylene-O—; or a covalent bond linking the 4 carbon ring to Ar;

2d) Ar is a substituted or unsubstituted C5-C60 aryl group;

3d) -L- is selected from the following: —O—; -alkylene-; -arylene-; —O-alkylene-; —O-arylene-; —O-alkylene-arylene-; —O-alkylene-O—; —O-alkylene-O-alkylene-O—; —O-arylene-O—; —O-alkylene-arylene-O—; —O—(CH2CH2-O)n-, wherein n is from 2 to 20; —O-alkylene-O-alkylene-; —O-alkylene-O-arylene-; —O-arylene-O—; —O-arylene-O-alkyene-; —O-arylene-O-arylene-; or a covalent bond linking 'Structure D" to "Structure A";

4di) the remaining $R^a_1$, $R^a_2$, $R^a_3$ and $R^a_4$ of one benzocyclobutene moiety are each, independently, selected from hydrogen, a hydrocarbon, a substituted hydrocarbon, a halogen, a cyano, a nitro, or a hydroxyl;

4dii) the remaining $R^a_1$, $R^a_2$, $R^a_3$ and $R^a_4$ of the other benzocyclobutene moiety are each, independently, selected from hydrogen, a hydrocarbon, a substituted hydrocarbon, a halogen, a cyano, a nitro, or a hydroxyl;

5di) $R^a_5$, $R^a_6$, $R^a_7$ or $R^a_8$ of one benzocyclobutene moiety are each, independently, selected from hydrogen, a hydrocarbon, a substituted hydrocarbon, a halogen, a cyano, a nitro, or a hydroxyl;

5dii) $R^a_5$, $R^a_6$, $R^a_7$ or $R^a_8$ of the other benzocyclobutene moiety are each, independently, selected from hydrogen, a hydrocarbon, a substituted hydrocarbon, a halogen, a cyano, a nitro, or a hydroxyl;

(Structure E)

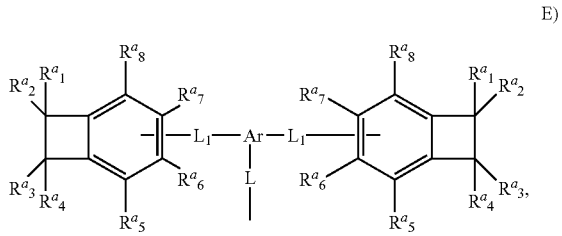

wherein

Structure E is connected to Structure A though -L-; wherein, for Structure E:

1ei) for one -L$_1$-, one of R$^a{}_5$, R$^a{}_6$, R$^a{}_7$ or R$^a{}_8$ of the benzocyclobutene moiety directly bonded to this -L$_1$-, is independently -L$_1$-; and wherein -L1- is selected from the following: —O—; -alkylene-; -arylene-; —O-alkylene-; —O-arylene-; —O-alkylene-arylene-; —O-alkylene-O—; —O-alkylene-O-alkylene-O—; —O-arylene-O—; —O— alkylene-arylene-O—; —O—(CH2CH2-O)n-, wherein n is from 2 to 20; —O-alkylene-O-alkylene-; —O-alkylene-O-arylene-; —O-arylene-O—; —O-arylene-O-alkyene-; —O-arylene-O-arylene-; or a covalent bond linking the 6-carbon ring to Ar;

1eii) for the other -L$_1$-, one of R$^a{}_5$, R$^a{}_6$, R$^a{}_7$ or R$^a{}_8$ of the other benzocyclo-butene moiety directly bonded to this -L$_1$-, is independently -L$_1$-; and wherein -L1- is selected from the following: —O—; -alkylene-; -arylene-; —O-alkylene-; —O-arylene-; —O-alkylene-arylene-; —O-alkylene-O—; —O-alkylene-O-alkylene-O—; —O-arylene-O—; —O-alkylene-arylene-O—; —O—(CH2CH2-O)n-, wherein n is from 2 to 20; —O— alkylene-O-alkylene-; —O-alkylene-O-arylene-; —O-arylene-O—; —O-arylene-O-alkyene-; —O-arylene-O-arylene-; or a covalent bond linking the 6-carbon ring to Ar;

2e) Ar is a substituted or unsubstituted C5-C60 aryl group; and

3e) -L- is selected from the following: —O—; -alkylene-; -arylene-; —O-alkylene-; —O-arylene-; —O-alkylene-arylene-; —O-alkylene-O—; —O-alkylene-O-alkylene-O—; —O-arylene-O—; —O-alkylene-arylene-O—; —O—(CH2CH2-O)n-, wherein n is from 2 to 20; —O-alkylene-O-alkylene-; —O-alkylene-O-arylene-; —O-arylene-O—; —O-arylene-O-alkyene-; —O-arylene-O-arylene-; or a covalent bond linking 'Structure E" to "Structure A";

4ei) the remaining R$^a{}_5$, R$^a{}_6$, R$^a{}_7$ or R$^a{}_8$ of one benzocyclobutene moiety are each, independently, selected from hydrogen, a hydrocarbon, a substituted hydrocarbon, a halogen, a cyano, a nitro, or a hydroxyl;

4eii) the remaining R$^a{}_5$, R$^a{}_6$, R$^a{}_7$ or R$^a{}_8$ of the other benzocyclobutene moiety are each, independently, selected from hydrogen, a hydrocarbon, a substituted hydrocarbon, a halogen, a cyano, a nitro, or a hydroxyl;

5ei) R$^a{}_1$, R$^a{}_2$, R$^a{}_3$ and R$^a{}_4$ of one benzocyclobutene moiety are each, independently, selected from hydrogen, a hydrocarbon, a substituted hydrocarbon, a halogen, a cyano, a nitro, or a hydroxyl;

5eii) R$^a{}_1$, R$^a{}_2$, R$^a{}_3$ and R$^a{}_4$ of the other benzocyclobutene moiety are each, independently, selected from hydrogen, a hydrocarbon, a substituted hydrocarbon, a halogen, a cyano, a nitro, or a hydroxyl; and wherein for Structure A, two or more R groups may optionally form one or more ring structures; and wherein for Structure A, one or more hydrogen atoms may be optionally substituted with deuterium.

DETAILED DESCRIPTION

Crosslinkable BCB-functionalized materials have been discovered, which mitigate the drawbacks discussed above, in conventional OLEDs applications. In terms of hole mobility, it has been discovered that the use of different attachment points on the HTL core, introducing BCB chemistry, can be utilized to tune the polymeric architecture after crosslink, and hence influence the flexibility of the HTL core. This approach should also allow for more effective stacking of the molecular cores, with respect to each other, which will increase the mobility of the hole in the HTL film, and improve device lifetime and efficiency. With different substitutions, such as alkyl, alkoxy, phenoxy, etc., on the four-member ring of BCB compound, the inventive composition, described herein, can also satisfy the solution-process conditions, with desirable curing temperature and curing times.

It has also been discovered that, the use of compositions containing BCB derivatives, as described herein, can used to form polymers. Also, the polymerization chemistry can occur at substantially lower temperatures, as compared to other chemical reactions of the art. With unsubstituted BCB derivatives, the ring opening temperatures has been noted to occur at temperatures ~250° C. (Kirchhoff, R. A.; Bruza, K. J. Progress in Polymer Science 1993, 18, 85-185). In this invention, the substitution of an oxygen donor results in a significant reduction in the ring opening temperatures to values from 100 to 120° C., which has significant process advantages over previous art.

Also, it has been discovered that, once a reactive o-quinodimethane moiety has been formed, Diels-Alder reactions can occur to generate new C—C bonds, in either a 1- or 2-component approach. In the case of a 2-component approach, the addition of an external polydienophiles can allow for full consumption of the reactive o-quinodimethane moieties, which allows for fewer reactive end groups. Reactive end-groups can introduce impurities into the HTL films, which can adversely affect device lifetime and efficiency. Also, Fréchet et al., discloses polystyrene with bis-(diarylamino)biphenyl and cross-linkable benzocyclobutene side groups use as hole-transport material, in solution-processed OLEDs (Chem. Mater. 2007, 19, 4827.). In contrast, it has been discovered the inventive compositions are crosslinkable materials with high molecular precision and high purity that will significantly benefit device performances.

As discussed above, the invention provides a composition comprising at least one compound selected from Structure A, as described above:

(Structure A)

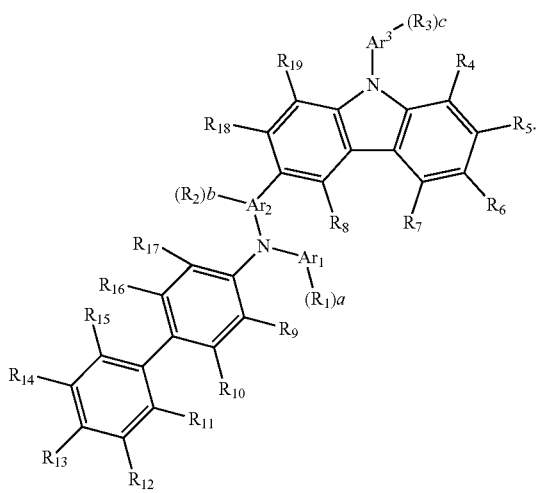

An inventive composition may comprise a combination of two or more embodiments as described herein.

Structure A may comprise a combination of two or more embodiments as described herein.

As used herein $R_1$=R1, $R_2$=R2, $R_3$=R3, and the like.

In one embodiment, Structure A is selected from Structure A-I as follows:

(Structure A-I)

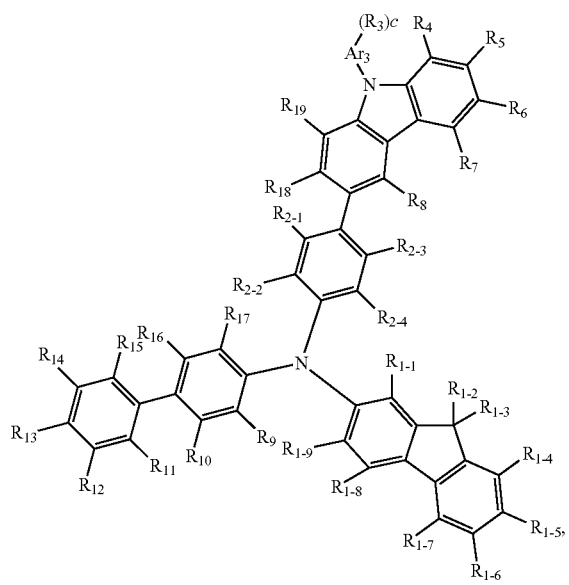

wherein $R_{2-1}$, $R_{2-2}$, $R_{2-3}$ and $R_{2-4}$ are each independently selected from the following: hydrogen, a hydrocarbon, a substituted hydrocarbon, a halogen, a cyano, a nitro, an alkoxy, or a hydroxyl; and wherein one of $R_{2-1}$, $R_{2-2}$, $R_{2-3}$ or $R_{2-4}$ is $(R_2)b$; and wherein $R_{1-1}$, $R_{1-4}$, $R_{1-5}$, $R_{1-6}$, $R_{1-7}$, $R_{1-8}$ and $R_{1-9}$ are each independently selected from the following: hydrogen, a hydrocarbon, a substituted hydrocarbon, a halogen, a cyano, a nitro, an alkoxy, or a hydroxyl; and wherein one of $R_{1-1}$, $R_{1-4}$, $R_{1-5}$, $R_{1-6}$, $R_{1-7}$, $R_{1-8}$ or $R_{1-9}$ is $(R_1)a$; and wherein $R_{1-2}$ and $R_{1-3}$ are each independently selected from the following: hydrogen, a hydrocarbon, a substituted hydrocarbon, or a halogen; and wherein groups $R_4$ to $R_{19}$ are each, independently, selected from hydrogen, a hydrocarbon, a substituted hydrocarbon, a halogen, a cyano, a nitro, an alkoxy, or a hydroxyl;

$Ar_3$ is selected from a substituted aryl, an unsubstituted aryl, a substituted heteroaryl, or an unsubstituted heteroaryl;

$(R_3)c$ is selected from hydrogen, a hydrocarbon, a substituted hydrocarbon, a halogen, a cyano, a nitro, an alkoxy, or a hydroxyl; and with the proviso that at least one of groups $(R_1)a$, $(R_2)b$, $(R_3)c$ or $R_4$ to $R_{19}$ is independently selected from Structure B, Structure C, or Structure D, or Structure E; and wherein for Structure A-I, two or more R groups may optionally form one or more ring structures; and wherein for Structure A-I, one or more hydrogen atoms may be optionally substituted with deuterium. In a further embodiment, a crosslinked polymer is formed from the composition comprising Structure A-I, and wherein the polymer comprises structural units selected from the following S1:

S1)

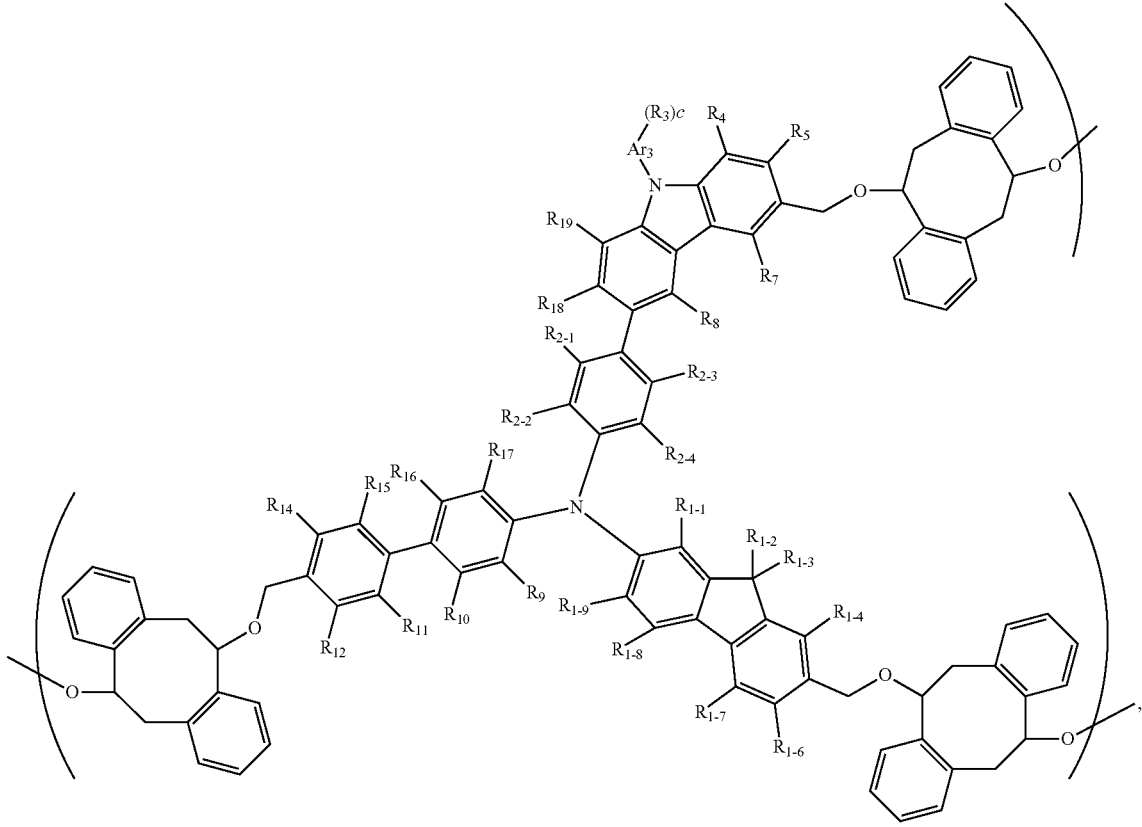

wherein n>1. In a further embodiment, for structure S1), $R_{2-1}$ to $R_{2-4}$ are each hydrogen. In a further embodiment, for structure S1), R9 to R12 and R14 to R17 are each hydrogen. The invention also provides a device comprising at least one film layer formed from the polymer comprising structural units S1).

In one embodiment, Structure A is selected from Structure A-II as follows:

(Structure A-II)

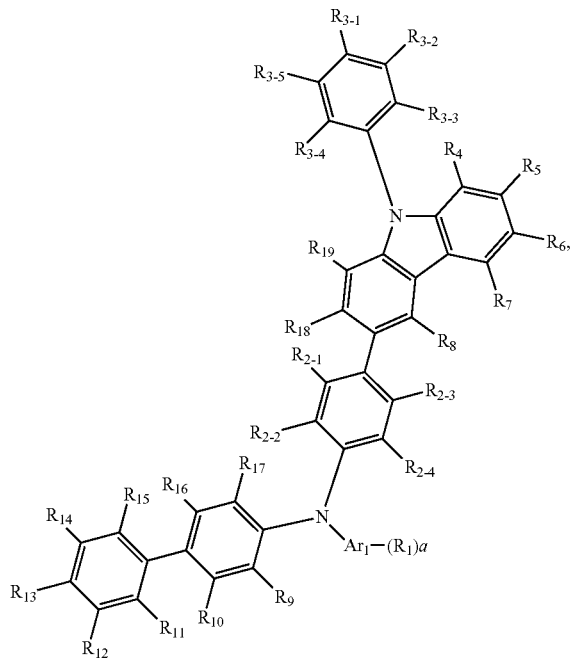

wherein $R_{2-1}$, $R_{2-2}$, $R_{2-3}$ and $R_{2-4}$ are each independently selected from the following: hydrogen, a hydrocarbon, a substituted hydrocarbon, a halogen, a cyano, a nitro, an alkoxy, or a hydroxyl; and wherein one of $R_{2-1}$, $R_{2-2}$, $R_{2-3}$ and $R_{2-4}$ is $(R_2)b$; and wherein $R_{3-1}$, $R_{3-2}$, $R_{3-3}$, $R_{3-4}$ and $R_{3-5}$ are each independently selected from the following: hydrogen, a hydrocarbon, a substituted hydrocarbon, a halogen, a cyano, a nitro, an alkoxy, or a hydroxyl; and wherein one of $R_{3-1}$, $R_{3-2}$, $R_{3-3}$, $R_{3-4}$ or $R_{3-5}$ is $(R_3)c$; and wherein groups $R_4$ to $R_{19}$ are each, independently, selected from hydrogen, a hydrocarbon, a substituted hydrocarbon, a halogen, a cyano, a nitro, an alkoxy, or a hydroxyl;

$Ar_1$ is selected from a substituted aryl, an unsubstituted aryl, a substituted heteroaryl, or an unsubstituted heteroaryl;

$(R_1)a$ is selected from hydrogen, a hydrocarbon, a substituted hydrocarbon, a halogen, a cyano, a nitro, an alkoxy, or a hydroxyl; and with the proviso that at least one of groups $(R_1)a$, $(R_2)b$, $(R_3)c$ or $R_4$ to $R_{19}$ is independently selected from Structure B, Structure C, or Structure D, or Structure E; and wherein for Structure A-II, two or more R groups may optionally form one or more ring structures; and wherein for Structure A-II, one or more hydrogen atoms may be optionally substituted with deuterium. In a further embodiment, a crosslinked polymer is formed from the composition comprising Structure A-II, and wherein the polymer comprises structural units selected from the following S2:

S2)

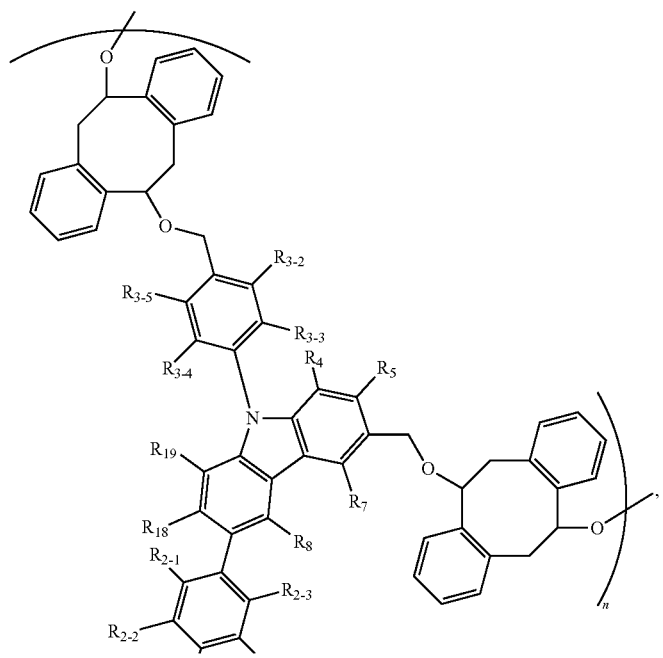

-continued

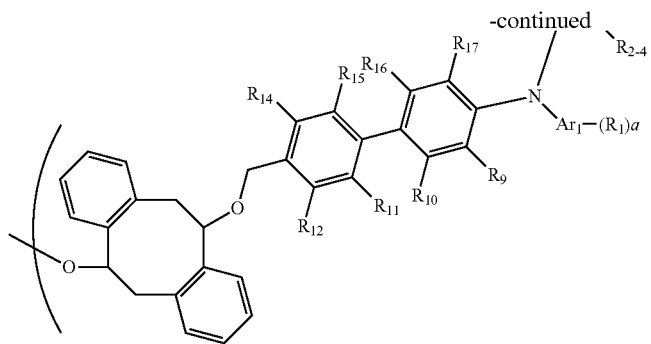

wherein n>1. In a further embodiment, for structure S2), $R_{2-1}$ to $R_{2-4}$ are each hydrogen. In a further embodiment, for structure S2), R9 to R12 and R14 to R17 are each hydrogen. The invention also provides a device comprising at least one film layer formed from the polymer comprising structural units S2).

In one embodiment, Structure A is selected from Structure A-III as follows:

(Structure A-III)

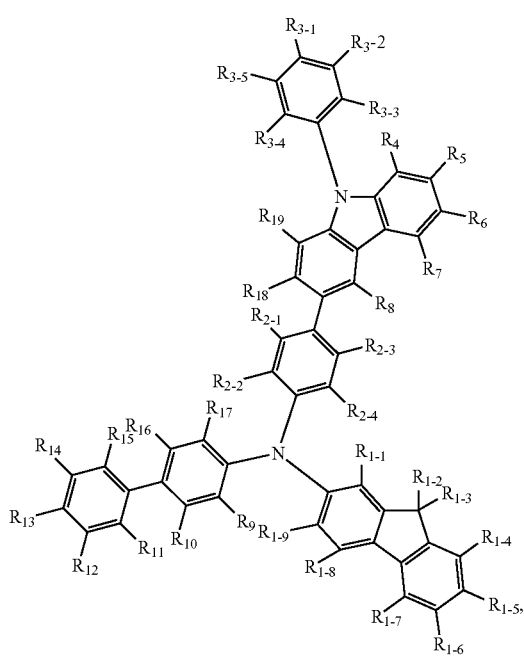

wherein $R_{2-1}$, $R_{2-2}$, $R_{2-3}$ and $R_{2-4}$ are each independently selected from the following: hydrogen, a hydrocarbon, a substituted hydrocarbon, a halogen, a cyano, a nitro, an alkoxy, or a hydroxyl; and wherein one of $R_{2-1}$, $R_{2-2}$, $R_{2-3}$ and $R_{2-4}$ is $(R_2)b$; and wherein $R_{1-1}$, $R_{1-4}$, $R_{1-5}$, $R_{1-6}$, $R_{1-7}$, $R_{1-8}$ and $R_{1-9}$ are each independently selected from the following: hydrogen, a hydrocarbon, a substituted hydrocarbon, a halogen, a cyano, a nitro, an alkoxy, or a hydroxyl; and wherein one of $R_{1-1}$, $R_{1-4}$, $R_{1-5}$, $R_{1-6}$, $R_{1-7}$, $R_{1-8}$ or $R_{1-9}$ is $(R_1)a$; and wherein $R_{1-2}$ and $R_{1-3}$ are each independently selected from the following: hydrogen, a hydrocarbon, a substituted hydrocarbon, or a halogen; and wherein $R_{3-1}$, $R_{3-2}$, $R_{3-3}$, $R_{3-4}$ and $R_{3-5}$ are each independently selected from the following: hydrogen, a hydrocarbon, a substituted hydrocarbon, a halogen, a cyano, a nitro, an alkoxy, or a hydroxyl; and wherein one of $R_{3-1}$, $R_{3-2}$, $R_{3-3}$, $R_{3-4}$ or $R_{3-5}$ is $(R_3)c$; and wherein groups $R_4$ to $R_{19}$ are each, independently, selected from hydrogen, a hydrocarbon, a substituted hydrocarbon, a halogen, a cyano, a nitro, an alkoxy, or a hydroxyl;

with the proviso that at least one of groups $(R_1)a$, $(R_2)b$, $(R_3)c$ or $R_4$ to $R_{19}$ is independently selected from Structure B, Structure C, or Structure D, or Structure E; and wherein for Structure A-III, two or more R groups may optionally form one or more ring structures; and wherein for Structure A-III, one or more hydrogen atoms may be optionally substituted with deuterium. In a further embodiment, a crosslinked polymer is formed from the composition comprising Structure A-III, and wherein the polymer comprises structural units selected from the following S3:

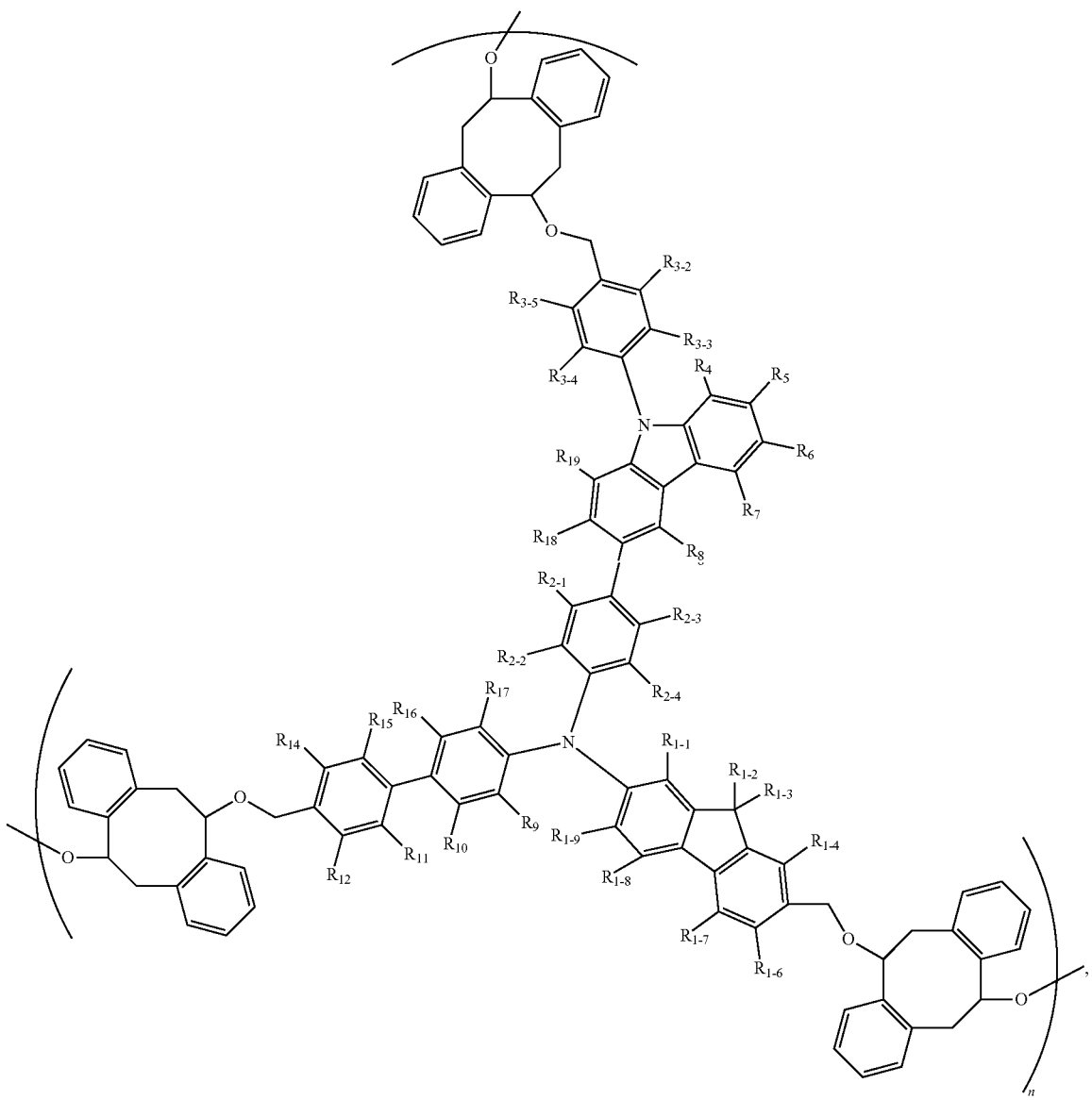

(S3)

wherein n>1. In a further embodiment, for structure S3), $R_{2-1}$ to $R_{2-4}$ are each hydrogen. In a further embodiment, for structure S3), R9 to R12 and R14 to R17 are each hydrogen. The invention also provides a device comprising at least one film layer formed from the polymer comprising structural units S3).

In one embodiment, at least one of groups $(R_1)a$, $(R_2)b$, $(R_3)c$ or $R_4$ to $R_{19}$ is independently selected from Structure B.

In one embodiment, for Structure B, -L- is selected from the following: —O—, -alkylene, —O-alkylene-, —O-phenylene-, —O-alkylene-phenylene-, or a covalent bond linking 'Structure B" to "Structure A".

In one embodiment, Structure B is selected from the following structures (i) or (ii):

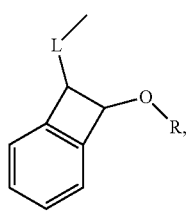

(ii)

or

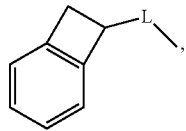
(i)

wherein R is hydrogen, a hydrocarbon or a substituted hydrocarbon.

In one embodiment, at least one of groups $(R_1)a$, $(R_2)b$, $(R_3)c$ or $R_4$ to $R_{19}$ is independently selected from Structure C.

In one embodiment, for Structure C, -L- is selected from the following: —O—, -alkylene, —O-alkylene-, —O-phenylene-, —O-alkylene-phenylene, or a covalent bond linking "Structure C" to "Structure A".

In one embodiment, Structure C is selected from the following structures (iii) or (iv):

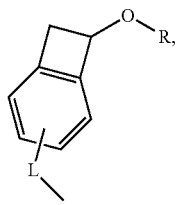
(iii)

wherein R is hydrogen, a hydrocarbon or a substituted hydrocarbon;

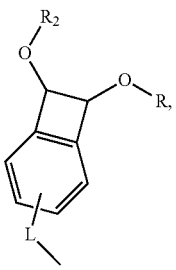
(iv)

wherein $R_1$ is hydrogen, a hydrocarbon or a substituted hydrocarbon; and $R_2$ is hydrogen, a hydrocarbon or a substituted hydrocarbon.

In one embodiment, at least one of groups $(R_1)a$, $(R_2)b$, $(R_3)c$ or $R_4$ to $R_{19}$ is independently selected from Structure D.

In one embodiment, Structure D is selected from the following structure (v):

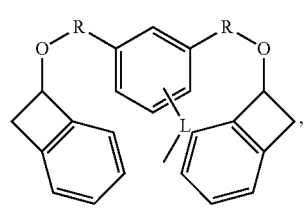
(v)

wherein each R is independently hydrogen, a hydrocarbon or a substituted hydrocarbon In one embodiment, for Structure A, R6-R11, R13-R17 and R18-R19 are each hydrogen.

In one embodiment, for Structure A, R9-R12 and R14-R17 are each hydrogen.

In one embodiment, for Structure A, R4, R5 and R13 are each hydrogen.

In one embodiment, Structure A is selected from the following structures (a) through (r):

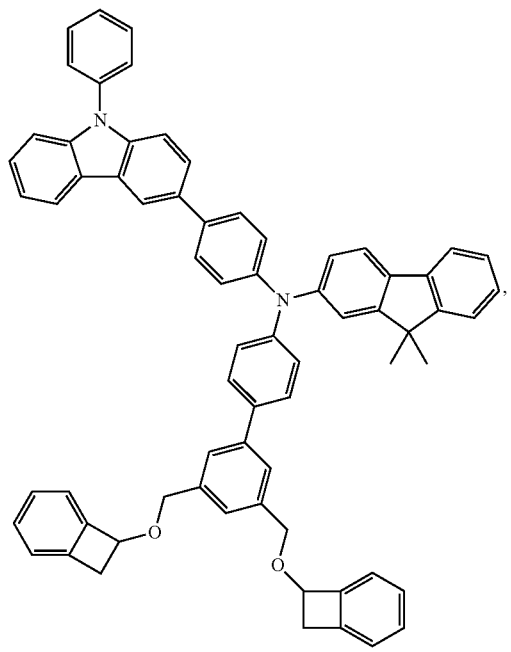
a

-continued
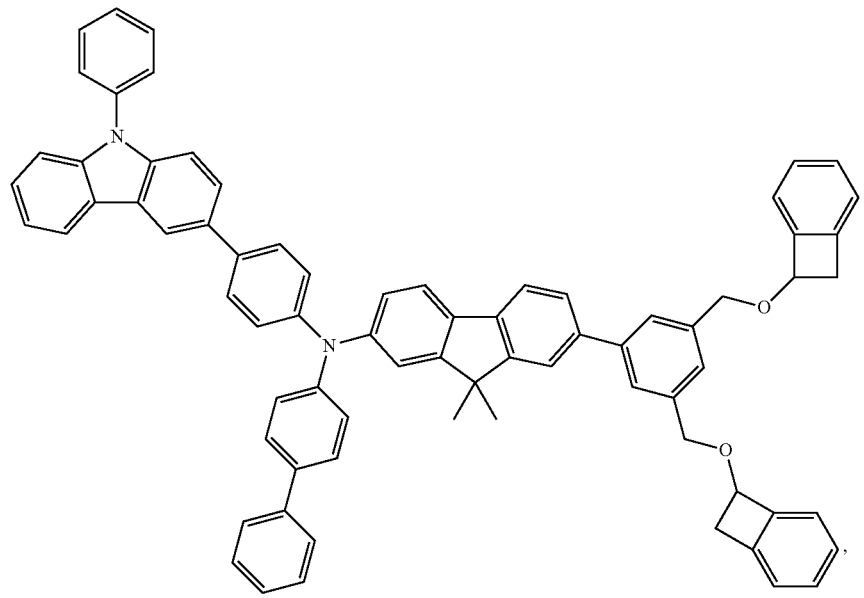
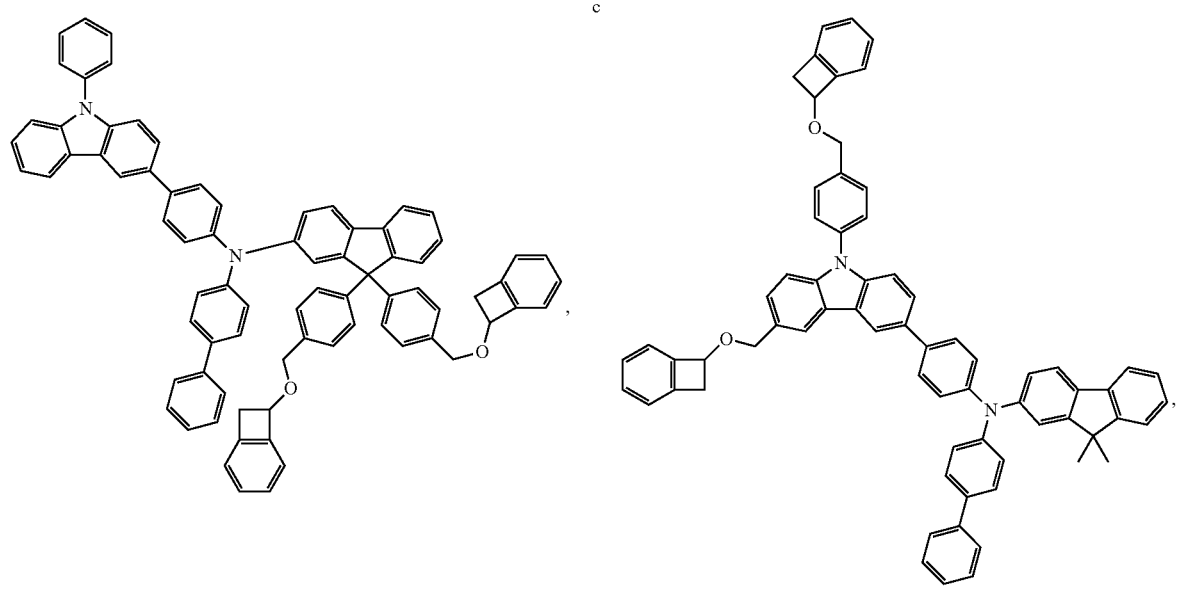

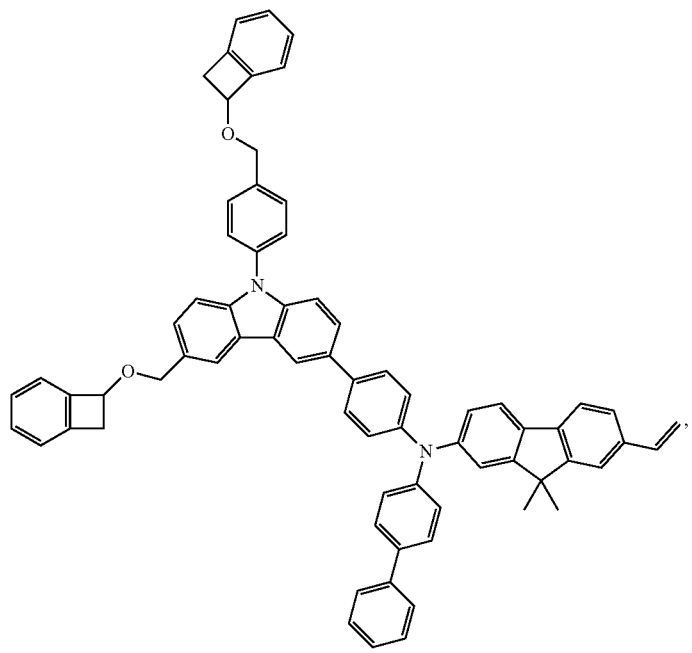
e
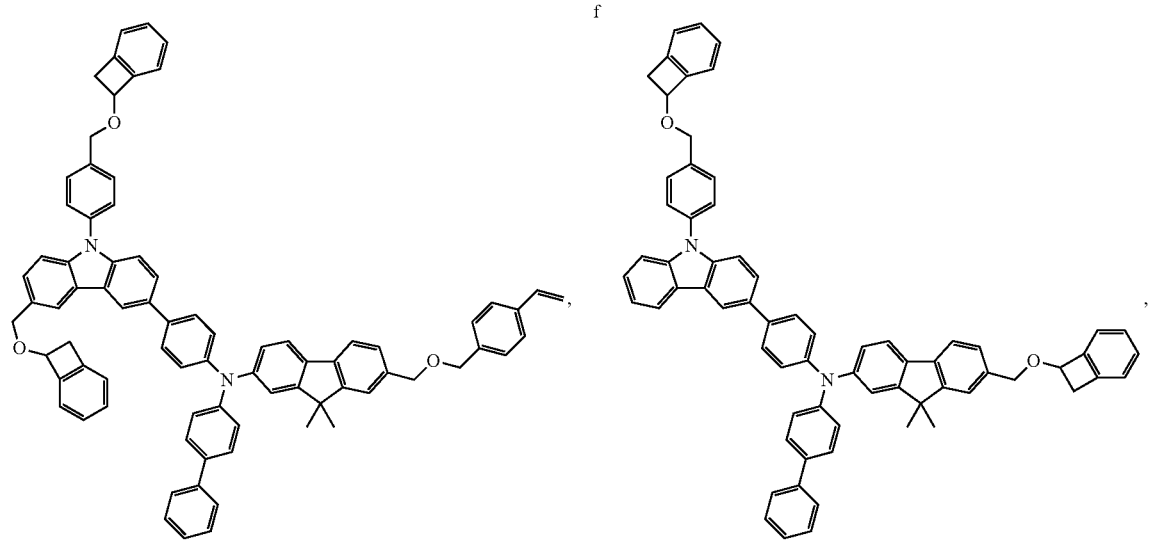

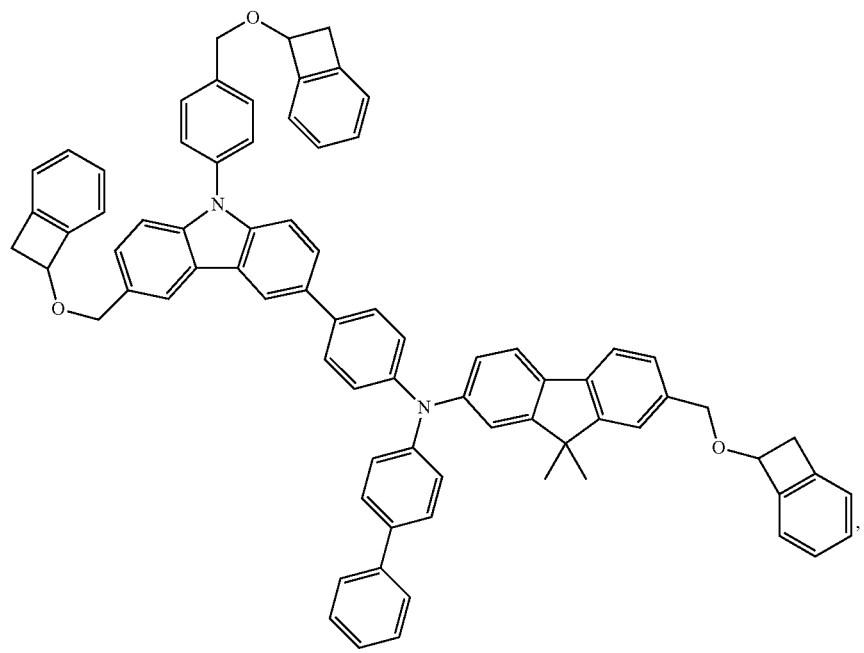
h
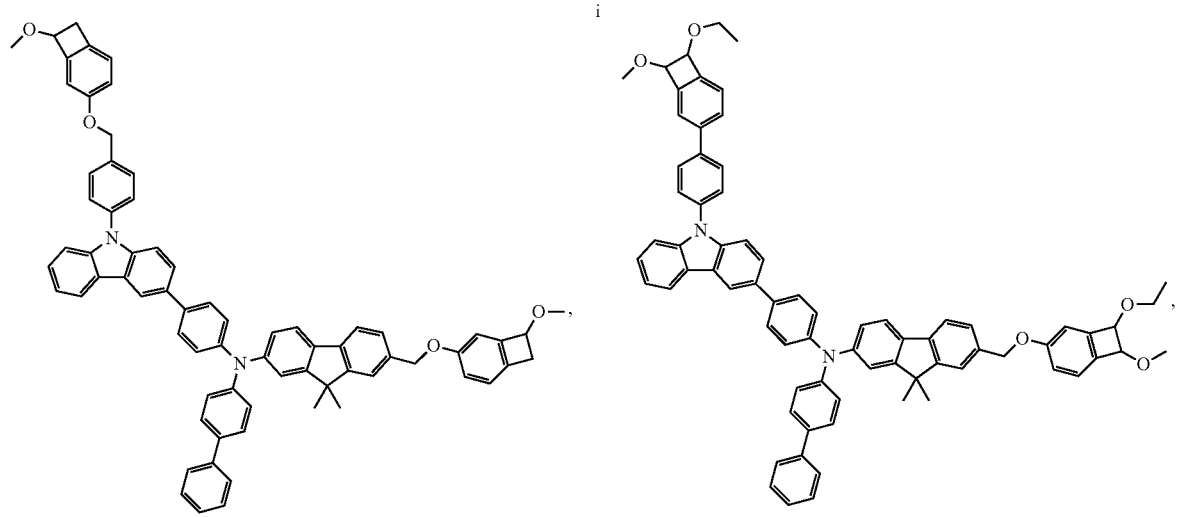
i
j

-continued
k
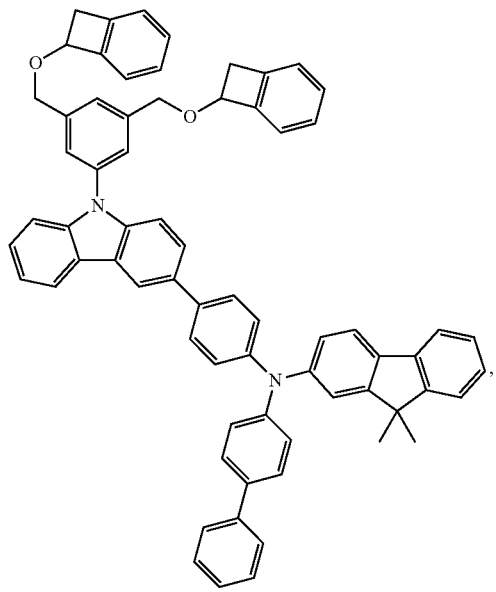
l
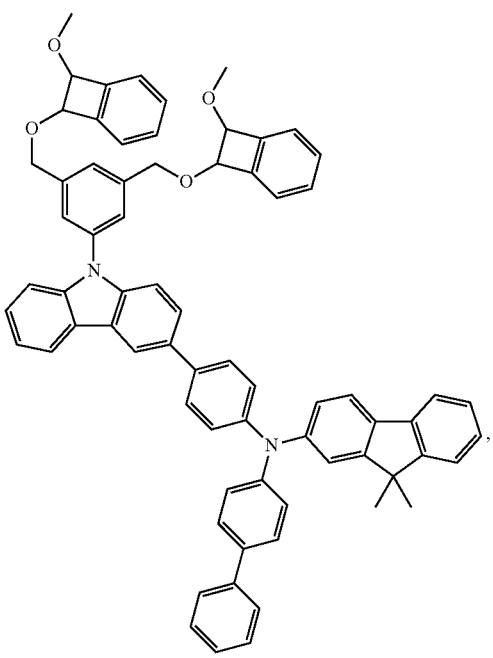
m
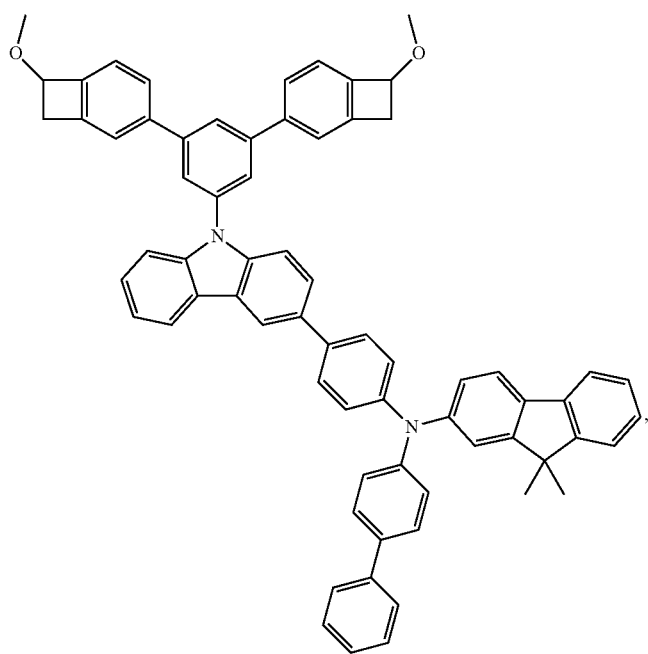

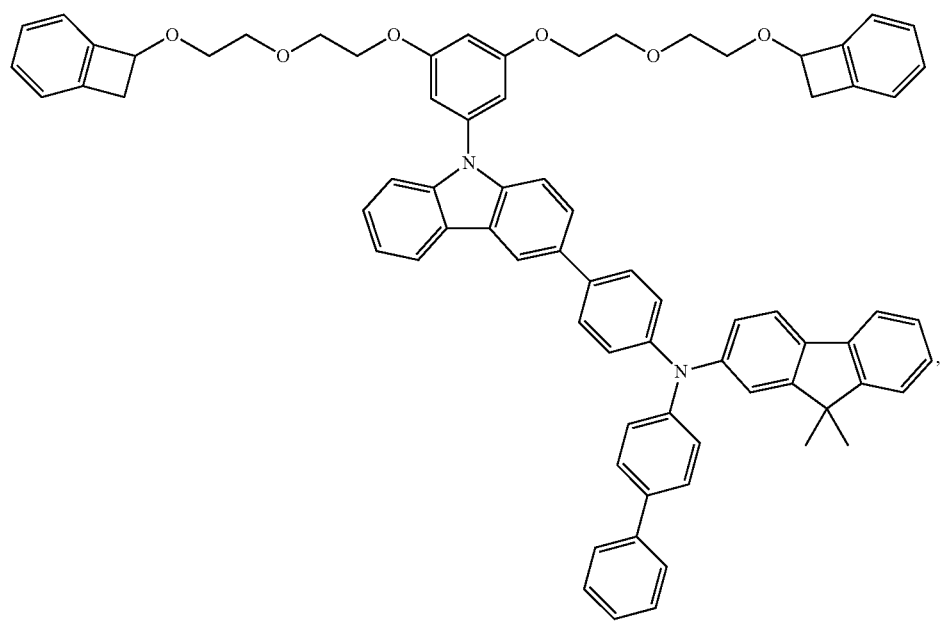
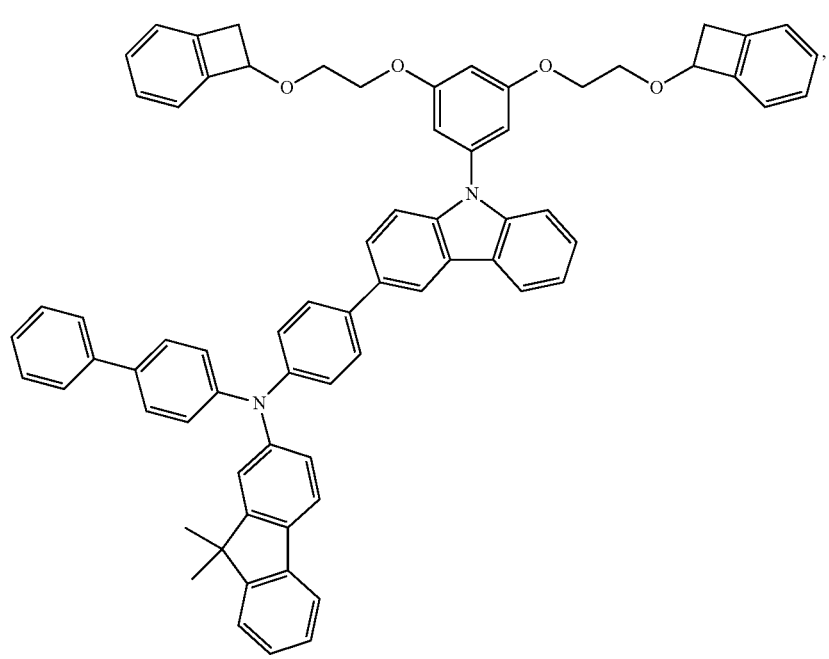

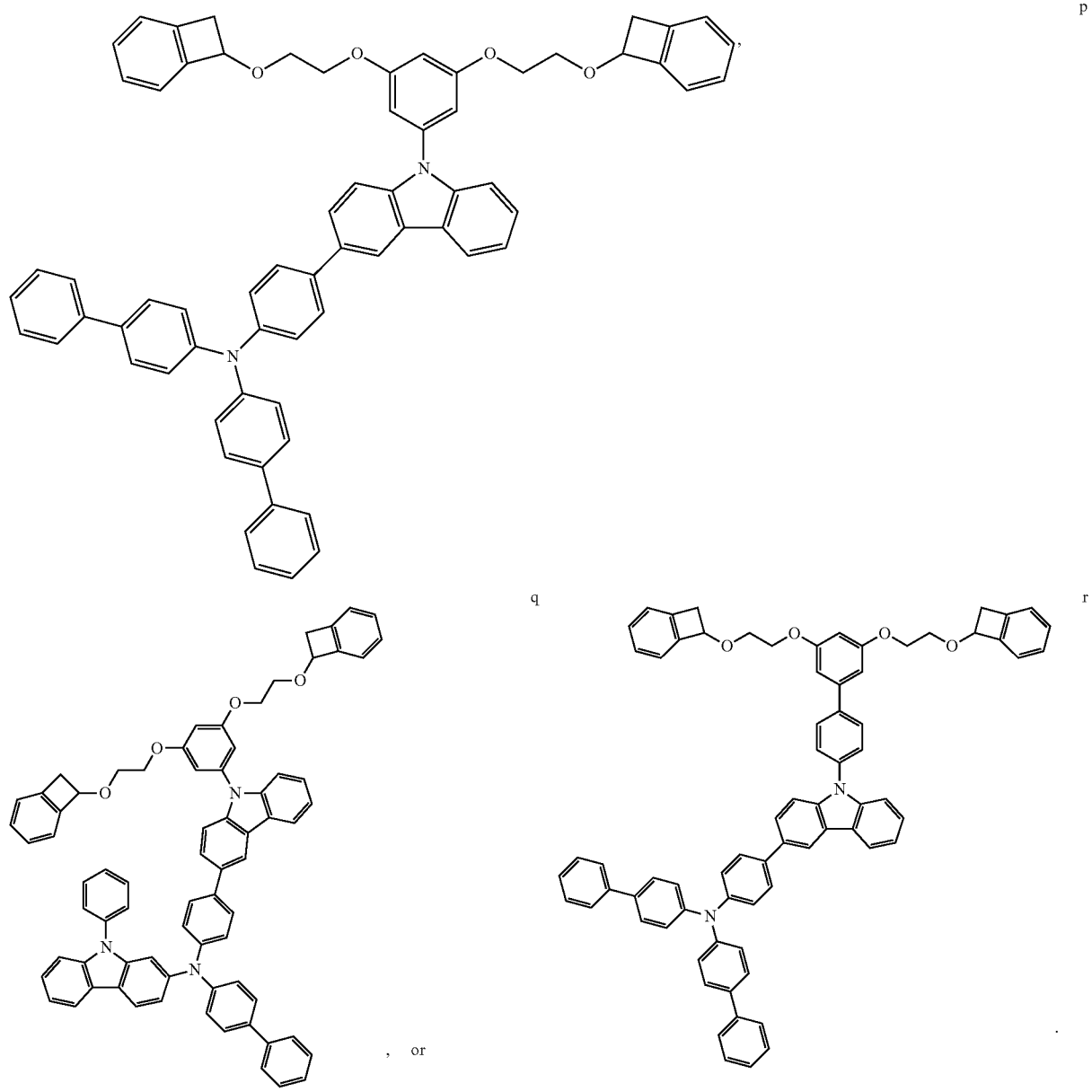

In one embodiment, Structure A has a molecular weight from 500 g/mole to 5000 g/mole, or from 500 g/mole to 2000 g/mole, or from 500 g/mole to 1000 g/mole.

In one embodiment, Structure A has a triplet energy from 2.30 eV to 3.20 eV.

In one embodiment, for Structure A, at least two of groups $(R_1)a$, $(R_2)b$, $(R_3)c$ or $R_4$ to $R_{19}$, and further at least two of groups $(R_1)a$, $(R_2)b$, $(R_3)c$, are each independently selected from the benzocyclobutene structures of Structure B, Structure C, Structure D, or Structure E.

In one embodiment, for Structure A, at least three of groups $(R_1)a$, $(R_2)b$, $(R_3)c$ or $R_4$ to $R_{19}$, and further at least three of groups $(R_1)a$, $(R_2)b$, $(R_3)c$, are each independently selected from the benzocyclobutene structures of Structure B, Structure C, Structure D, or Structure E.

In one embodiment, two of groups $(R_1)a$, $(R_2)b$, $(R_3)c$ or $R_4$ to $R_{19}$, and further two of groups $(R_1)a$, $(R_2)b$, $(R_3)c$, are each independently selected from the benzocyclobutene structures of Structure B, Structure C, Structure D, or Structure E.

In one embodiment, three of groups $(R_1)a$, $(R_2)b$, $(R_3)c$ or $R_4$ to $R_{19}$, and further three of groups $(R_1)a$, $(R_2)b$, $(R_3)c$, are each independently selected from the benzocyclobutene structures of Structure B, Structure C, Structure D, or Structure E.

In one embodiment, for Structure A, two or more R groups do not form one or more ring structures.

In one embodiment, for Structure A, one or more hydrogen atoms are not optionally substituted with deuterium.

The invention also provides a film comprising at least one Layer A formed from an inventive composition.

An inventive film may comprise a combination of two or more embodiments described herein.

The invention also provides an article comprising at least one component formed from an inventive composition.

In one embodiment, the article is an electroluminescent device.

The invention also provides an article comprising at least one component formed from an inventive film.

In one embodiment, the article is an electroluminescent device.

The invention also provides an electroluminescent device comprising at least one component formed from an inventive composition.

An inventive article may comprise a combination of two or more embodiments described herein.

An inventive device may comprise a combination of two or more embodiments described herein.

In one embodiment, the inventive composition comprises at least one deuterium atom.

In one embodiment, the compound of Structure A has a purity greater than 99 percent.

In one embodiment, the composition comprises at least two compounds selected from Structure A.

Structure A may comprise a combination of two or more embodiments described herein.

In one embodiment, the composition comprises from 50 to 90 weight percent of at least one compound selected from Structure A, based on the weight of the composition. In a further embodiment, the composition comprises from 70 to 90 weight percent, further from 90 to 99 weight percent of at least one compound selected from Structure A, based on the weight of the composition.

In one embodiment, the composition further comprises an organometal compound, and further a metal quinolate. In a further embodiment, the metal quinolate is a lithium quinolate with or without substituents.

In one embodiment, the organometal compound comprises lithium. In a further embodiment, the organometal is lithium quinolate with or without substituents.

In one embodiment, the weight ratio of at least one compound of Structure A to the organometal compound is from 9/1 to 1/1, further from 4/1 to 1/1, further from 3/2 to 1/1. In a further embodiment, the organometal compound is a metal quinolate. In a further embodiment, the metal quinolate is a lithium quinolate with or without substituents An inventive composition may comprise a combination of two or more embodiments described herein.

Definitions

The term "hydrocarbon," as used herein, refers to a chemical group containing only hydrogen and carbon atoms.

The term "substituted hydrocarbon," as used herein, refers to a hydrocarbon in which at least one hydrogen atom is substituted with a heteroatom or a chemical group containing at least one heteroatom. Heteroatoms include, but are not limited to, O, N, P and S. Substituents include, but are not limited to, OR', $NR'_2$, $PR'_2$, $P(=O)R'_2$, $SiR'_3$; where each R' is a $C_1$-$C_{20}$ hydrocarbyl group. The valency of a hydrocarbyl group (mono, di, etc.) can be determined by the chemical structure of the molecule comprising the hydrocarbyl group.

The term "aryl," as described herein, refers to an organic radical derived from aromatic hydrocarbon by deleting one hydrogen atom therefrom. An aryl group may be a monocyclic and/or fused ring system, each ring of which suitably contains from 4 to 7, preferably from 5 or 6 atoms. Structures wherein two or more aryl groups are combined through single bond(s) are also included. Specific examples include, but are not limited to, phenyl, naphthyl, biphenyl, anthryl, indenyl, fluorenyl, benzofluorenyl, phenanthryl, triphenylenyl, pyrenyl, perylenyl, chrysenyl, naphtacenyl, fluoranthenyl and the like, but are not restricted thereto. The naphthyl may be 1-naphthyl or 2-naphthyl, the anthryl may be 1-anthryl, 2-anthryl or 9-anthryl, and the fluorenyl may be any one of 1-fluorenyl, 2-fluorenyl, 3-fluorenyl, 4-fluorenyl and 9-fluorenyl. As used herein, aryl includes monovalent, divalent, or higher valent groups. The valency of an aryl can be determined by the chemical structure of the molecule comprising the aryl.

The term "substituted aryl," as used herein, refers to an aryl in which at least one hydrogen atom is substituted with a heteroatom or a chemical group containing at least one heteroatom. Heteroatoms include, but are not limited to, O, N, P and S. Substituents include, but are not limited to, OR', $NR'_2$, $PR'_2$, $P(=O)R'_2$, $SiR'_3$; where each R' is a $C_{30}$-$C_{100}$ hydrocarbyl group.

The term "heteroaryl," as described herein, refers to an aryl group, in which at least one carbon atom or CH group or $CH_2$ is substituted with a heteroatom (for example, B, N, O, S, P(=O), Si and P) or a chemical group containing at least one heteroatom. The heteroaryl may be a 5- or 6-membered monocyclic heteroaryl or a polycyclic heteroaryl which is fused with one or more benzene ring(s), and may be partially saturated. The structures having one or more heteroaryl group(s) bonded through a single bond are also included. The heteroaryl groups may include divalent aryl groups of which the heteroatoms are oxidized or quarternized to form N-oxides, quaternary salts, or the like. Specific examples include, but are not limited to, monocyclic heteroaryl groups, such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl; polycyclic heteroaryl groups, such as benzofuranyl, fluoreno[4, 3-b]benzofuranyl, benzothiophenyl, fluoreno[4, 3-b]benzothiophenyl, isobenzofuranyl, benzimidazolyl, benzothiazolyl, benzisothiazolyl, benzisoxazolyl, benzoxazolyl, isoindolyl, indolyl, indazolyl, benzothia-diazolyl, quinolyl, isoquinolyl, cinnolinyl, quinazolinyl, quinoxalinyl, carbazolyl, phenanthridinyl and benzodioxolyl; and corresponding N-oxides (for example, pyridyl N-oxide, quinolyl N-oxide) and quaternary salts thereof. As used herein, heteroaryl includes monovalent, divalent, or higher valent groups. The valency of a heteroaryl can be determined by the chemical structure of the molecule comprising the heteroaryl.

The term "substituted heteroaryl," as used herein, refers to a heteroaryl in which at least one hydrogen atom is substituted with a heteroatom or a chemical group containing at least one heteroatom. Heteroatoms include, but are not limited to, O, N, P and S. Substituents include, but are not limited to, OR', $NR'_2$, $PR'_2$, $P(=O)R'_2$, $SiR'_3$; where each R' is a $C_1$-$C_{20}$ hydrocarbyl group.

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into and/or within the polymer structure), and the term interpolymer as defined hereinafter.

The term "interpolymer," as used herein, refers to polymers prepared by the polymerization of at least two different types of monomers. The generic term interpolymer thus includes copolymers (employed to refer to polymers prepared from two different types of monomers), and polymers prepared from more than two different types of monomers.

Experimental

Reagents and Test Methods

All solvents and reagents were obtained from commercial vendors, and were used in the highest available purities, and/or when necessary, recrystallized before use. Dry solvents were obtained from in-house purification/dispensing system (hexane, toluene, and tetrahydrofuran), or purchased from Sigma-Aldrich. All experiments involving "water sensitive compounds" were conducted in "oven dried" glassware, under nitrogen atmosphere, or in a glovebox. Reactions were monitored by analytical, thin-layer chromatography (TLC) on precoated aluminum plates (VWR 60 F254), and visualized by UV light and/or potassium permanganate staining. Flash chromatography was performed on an ISCO COMBIFLASH system with GRACERESOLV cartridges.

Modeling

All computations utilized the Gaussian09 program[1]. The calculations were performed with the hybrid density functional theory (DFT) method, B3LYP,[2] and the 6-31G* (5d) basis set.[3] The singlet state calculations used the closed shell approximation, and the triplet state calculations used the open shell approximation. All values are quoted in electron-volts (eV). The HOMO and LUMO values were determined from the orbital energies of the optimized geometry of the singlet ground state. The triplet energies were determined as the difference between the total energy of the optimized triplet state and the optimized singlet state.

1. Gaussian 09, Revision A.02, Frisch, M. J.; Trucks, G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenberg, J. L.; Hada, M.; Ehara, M.; Toyota, K.; Fukuda, R.; Hasegawa, J.; Ishida, M.; Nakajima, T.; Honda, Y.; Kitao, O.; Nakai, N.; Vreven, T.; Montgomery, Jr., J. A.; Peralta, J. E.; Ogliaro, F.; Bearpark, M.; Heyd, J. J.; Brothers, E.; Kudin, K. N.; Staroverov, V. N.; Kobayashi, R.; Normand, J.; Raghavachari, K.; Rendell, A.; Burant, J. C.; Iyengar, S. S.; Tomasi, J.; Cossi, M.; Rega, N.; Millam, J. M.; Klene, M.; Knox, J. E.; Cross, J. B.; Bakken, V.; Adamo, C.; Jaramillo, J.; Gomperts, R.; Stratmann, R. E.; Yazyev, O.; Austin, A. J.; Cammi, R.; Pomelli, C.; Ochterski, J. W.; Martin, R. L.; Morokuma, K.; Zakrzewski, V. G.; Voth, G. A.; Salvador, P.; Dannenberg, J. J.; Dapprich, S.; Daniels, A. D.; Farkas, O.; Foresman, J. B.; Ortiz, J. V.; Cioslowski, J.; Fox, D. J., Gaussian, Inc., Wallingford Conn., 2009.

2. (a) Becke, A. D. *J. Chem. Phys.* 1993, 98, 5648. (b) Lee, C.; Yang, W.; Parr, R. G. *Phys. Rev B* 1988, 37, 785. (c) Miehlich, B.; Savin, A.; Stoll, H.; Preuss, H. *Chem. Phys. Lett.* 1989, 157, 200.

3. (a) Ditchfield, R.; Hehre, W. J.; Pople, J. A. *J. Chem. Phys.* 1971, 54, 724. (b) Hehre, W. J.; Ditchfield, R.; Pople, J. A. *J. Chem. Phys.* 1972, 56, 2257. (c) Gordon, M. S. *Chem. Phys. Lett.* 1980, 76, 163.

NMR:

The 1H NMR spectra were recorded on a Varian Mercury Plus 400 MHz spectrometer. Chemical shifts were reported versus tetramethylsilane (TMS) in CDCl$_3$.

LC/MS:

Sample was dissolved in THF at around 1 mg/mL. 1 μL solution was injected for LC/MS analysis.

Instrument: Agilent 1220 HPLC/G6224A TOF mass spectrometer

Column: Agilent eclipse-C18 4.6*50 mm, 1.7 um

Column oven temperature: 30 Deg C.

Solvent: A: THF; B: 0.1% FA in water/ACN 95/5

Gradient: 0-6 min 40-80% A, hold for 9 min

Flow: 0.3 mL/min

UV detector: Diode Array 254 nm

MS Condition:

Capillary Voltage: 3900 kV (Neg), 3500 kV (Pos)

Mode: Neg and Pos

Scan: 100-2000 amu

Rate: 1 s/scan

Desolvation temperature: 300 deg C.

HPLC:

Approximately 1 mg of the samples weighed then was diluted with 1 mL tetrahydro-furan. The sample solution was at last filtrated through a 0.45 μm syringe filter and 5 μl of the filtrate was injected to HPLC system.

| Time | A % | B % | Flow Rate (mL/min) |
|---|---|---|---|
| 0.0 | 42 | 58 | 1 |
| 40 | 35 | 65 | 1 |
| 47 | 34 | 66 | 1 |
| 48 | 10 | 90 | 1 |

1) Materials and Synthesis

Materials used in this study are shown in Tables 1A and 1B.

TABLE 1A

| Materials | | | |
|---|---|---|---|
| Material name | Chemical structure | Supplier | Note |
| Bromobenzene | 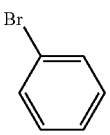 | SCRC | A.R. |

TABLE 1A-continued

Materials

| Material name | Chemical structure | Supplier | Note |
|---|---|---|---|
| 4-bromobenzaldehyde | (4-bromobenzaldehyde structure) | SCRC | A.R. |
| 9H-carbazole | (9H-carbazole structure) | SCRC | A.R. |
| N-([1,1'-biphenyl]-4-yl)-9,9-dimethyl-9H-fluoren-2-amine | (structure) | SCRC | A.R. |
| Titanium tetrachloride | $TiCl_4$ | SCRC | A.R. |
| Tris(dibenzylideneacetone)dipalladium(0) | $Pd(OAc)_2$ | Shanghai Darui Fine Chemicals | A.R. |
| Tetrakis(triphenylphosphine)palladium | $Pd(PPh_3)_4$ | Shanghai Darui Fine Chemicals | A.R. |
| [1,1'-Bis(diphenylphosphino)ferrocene]-palladium(II) chloride | $Pd(dppf)Cl_2$ | Shanghai Darui Fine Chemicals | A.R. |
| 2-(Dicyclohexylphosphino)-2',4',6'-triisopropylbiphenyl (X-Phos) | (structure) | Shang hai Demo Medical Tech Co. Ltd. | A.R. |

A.R. = Analytical Reagent

TABLE 1B

Materials

| Material name | Chemical structure | Supplier | Note |
|---|---|---|---|
| 4,4,4',4',5,5,5',5'-octamethyl-2,2'-bi(1,3,2-dioxaborolane) | (structure) | SCRC | A.R. |
| N-Bromosuccinimide | NBS | SCRC | A.R. |
| Cuprous Iodide |  | SCRC | A.R. |
| Sodium hydride (NaH) |  | TCI | A.R. |
| Sodium borohydride (NaBH$_4$) |  | SCRC | A.R. |
| Potassium carbonate |  | SCRC | A.R. |
| Potassium tert-butoxide (tBuOK) |  | TCI | A.R. |
| Potassium Acetate (KOAc) |  | SCRC | A.R. |

TABLE 1B-continued

Materials

| Material name | Chemical structure | Supplier | Note |
|---|---|---|---|
| dichloro(methoxy)methane |  | SCRC | A.R. |
| Dimethylformamide |  | SCRC | A.R. |
| 1,4-dioxane |  | SCRC | A.R. |
| Dichloromethane |  | SCRC | A.R. |
| Tetrahydrogenfuran |  | SCRC | A.R. |
| Toluene |  | SCRC | A.R. |

A.R. = Analytical Reagent

Syntheses

Synthesis of N-([1,1'-biphenyl]-4-yl)-9,9-dimethyl-N-phenyl-9H-fluoren-2-amine (1)

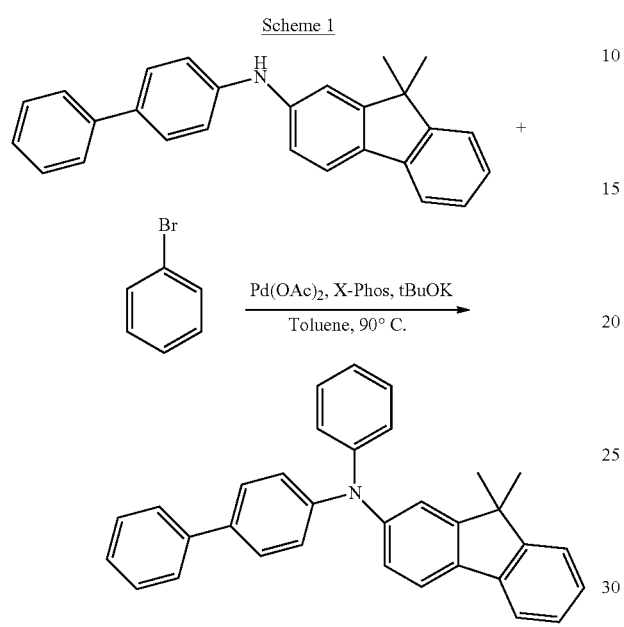

N-([1,1'-biphenyl]-4-yl)-9,9-dimethyl-9H-fluoren-2-amine (40.0 g, 110 mmol), bromobenzene (23.4 g, 150 mmol), Pd(OAc)$_2$ (616 mg, 2.75 mmol), X-Phos (1.57 g, 3.3 mmol), tBuOK (24.6 g, 220 mmol) were added into a 250 mL, three-necked round-bottom flask, equipped with a reflux condenser. After addition of 250 mL dry toluene, under N$_2$ atmosphere, the suspension was heated to 90° C., and stirred overnight under a flow of N$_2$. After cooling to room temperature, water was added, and the organic layer was separated. The solvent was evaporated under vacuum, and the residue was used for the next step without further purification (yield: 95%). MS (ESI): 437.02 [M+H]$^+$.

Synthesis of N-([1,1'-biphenyl]-4-yl)-N-(4-bromophenyl)-9,9-dimethyl-9H-fluoren-2-amine (2)

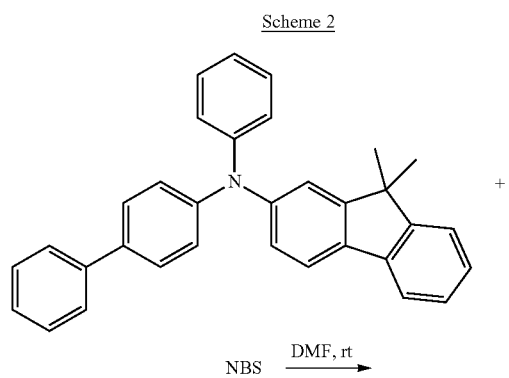

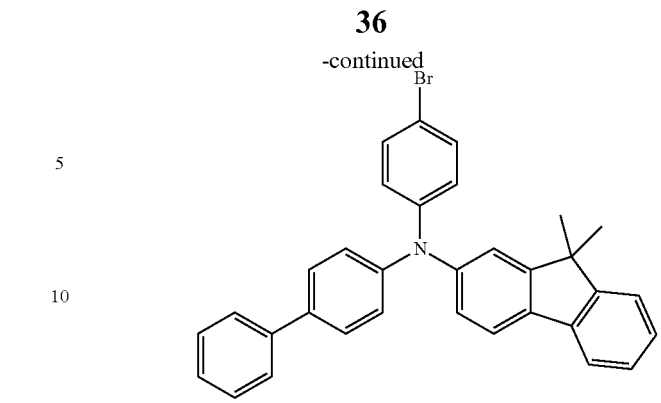

To a solution of N-([1,1'-biphenyl]-4-yl)-9,9-dimethyl-N-phenyl-9H-fluoren-2-amine (1) (35.0 g, 80 mmol) in 150 mL DMF, N-bromosuccinimide (NBS) (16.02 g, 90 mmol), in 100 mL DMF, was added dropwise in 30 minutes. After addition, the mixture was stirred at room temperature for 12 hours, and then poured into water to precipitate. The solid was filtered, and recrystallized from dichloromethane and ethanol to give white solid (yield: 92%). MS (ESI): 516.12 [M+H]$^+$.

Synthesis of 7-([1,1'-biphenyl]-4-yl(4-bromophenyl)amino)-9,9-dimethyl-9H-fluorene-2-carbaldehyde (3)

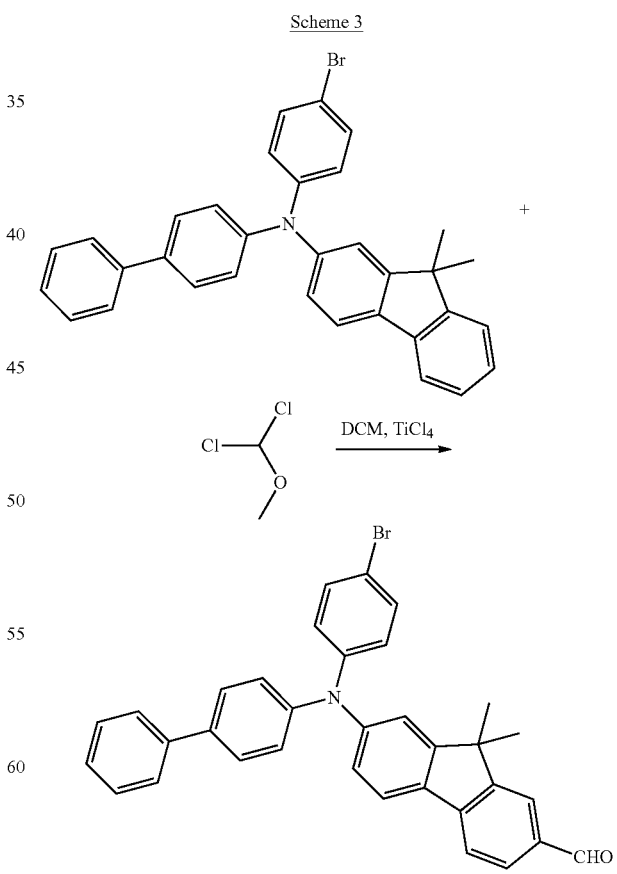

To a solution of triarylamine (25.8 g, 50 mmol) in 100 mL CH$_2$Cl$_2$ at 0° C., TiCl$_4$ (54.6 mL, 500 mmol), diluted with 100 mL CH$_2$Cl$_2$, were added in 30 minutes. The mixture was stirred for an additional 30 minutes at 0° C. Then, CH$_3$OCHCl$_2$ (27.0 mL, 300 mmol), in 200 mL of CH$_2$Cl$_2$, was added dropwise in 30 minutes. The dark-green solution was stirred for another one hour at 0° C. After completion, water, with crushed ice, was slowly added to quench the reaction. The organic layer was separated, and washed consecutively with saturated sodium bicarbonate solution, brine, and dried over anhydrous sodium sulphate. After filtration, the solvent was removed under vacuum, and the residue was purified through column chromatography to give crude product (yield: 55%). MS (ESI): 544.12 [M+H]$^+$.

Synthesis of 4-(9H-carbazol-9-yl)benzaldehyde (4)

Scheme 4

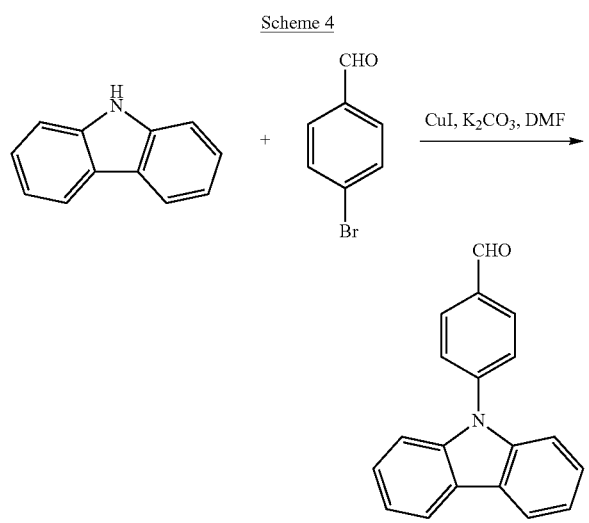

A mixture of 9H-carbazole (9.53 g, 57 mmol), 4-bromobenzaldehyde (21.1 g, 114 mmol), Copper(I) iodide (1.80 g, 9.4 mmol), K$_2$CO$_3$ (11.8 g, 86 mmol), in 60 mL dry DMF, was heated to 140° C., under nitrogen atmosphere for 12 hours. After cooling to room temperature, the inorganic solid was filtered, and the residue was poured into ice water to precipitate the product. The so-formed solid was collected, and washed by water, ethanol several times, then crystallized from CH$_2$Cl$_2$ and ethanol, to give light-yellow solid (yield: 95%). MS (ESI): 272.10 [M+H]$^+$.

Synthesis of 4-(3-bromo-9H-carbazol-9-yl)benzaldehyde (5)

Scheme 5

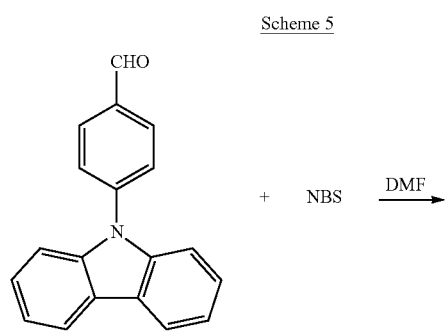

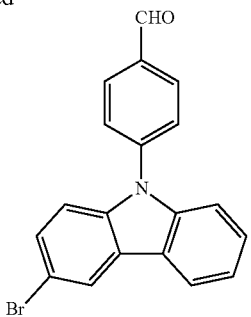

To a solution of 4-(9H-carbazol-9-yl)benzaldehyde (26.6 g, 98 mmol) in 100 mL DMF, NBS (17.4 g, 98 mmol), in 100 mL DMF, was added dropwise in 30 minutes. After addition, the mixture was stirred at room temperature for 12 hours. The solution was poured into ice water to precipitate the product. After filtration, the solid was collected, and washed by water, ethanol several times, then dried under vacuum, and used for the next step without further purification (yield: 96%). MS (ESI): 350.01 [M+H]$^+$.

Synthesis of 4-(3-(4,4,5,5-tetramethyl-1,3,2-dioxaborolan-2-yl)-9H-carbazol-9-yl)benzaldehyde (6)

Scheme 6

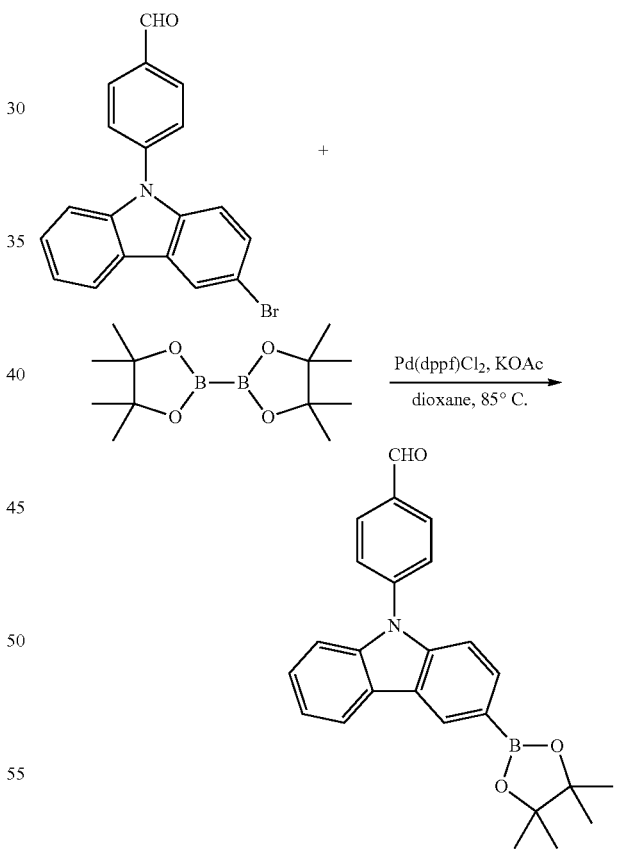

A mixture of 3-bromo-9-(4-formylphenyl)-9H-carbazole (10.51 g, 30 mmol), 4,4,4',4',5,5,5',5'-octamethyl-2,2'-bi(1,3,2-dioxaborolane) (9.14 g, 36 mmol, 253), Pd(dppf)$_2$Cl$_2$ (571 mg, 0.75 mmol), CH$_3$COOK (4.41 g, 45 mmol), and 60 mL of dry dioxane, was heated at 85° C., under nitrogen atmosphere for 12 hours. After cooling to room temperature, the solvent was removed under vacuum, and then water was added. The mixture was extracted with CH$_2$Cl$_2$. The organic layer was collected, and dried over anhydrous sodium sulphate. After filtration, the filtrate was evaporated to remove solvent, and the residue was purified through column chromatography on silica gel, to give white solid (yield: 84%). MS (ESI): 398.16 [M+H]⁺.

Synthesis of 7-([1,1'-biphenyl]-4-yl(4-(9-(4-formyl-phenyl)-9H-carbazol-3-yl)phenyl)amino)-9,9-dimethyl-9H-fluorene-2-carbaldehyde (7)

A mixture of 6 (0.7 g, 1.76 mmol), 3 (0.8 g, 1.47 mmol), Pd(PPh$_3$)$_4$ (76 mg, 0.064 mmol), 2M K$_2$CO$_3$ (0.8 g, 6 mmol, 3 mL H$_2$O), 3 mL ethanol and 3 mL of toluene, was heated at 90° C., under nitrogen atmosphere for 12 hours. After cooling to room temperature, the solvent was removed under vacuum, and the residue was dissolved with CH$_2$Cl$_2$. The organic layer was washed with water, and then dried over anhydrous sodium sulphate. After filtration, the filtrate was evaporated to remove solvent, and the residue was purified through column chromatography on silica gel, to give white solid (yield: 85%). MS (ESI): 735.29 [M+H]⁺.

Synthesis of (7-([1,1'-biphenyl]-4-yl(4-(9-(4-(hydroxymethyl)phenyl)-9H-carbazol-3-yl)phenyl)amino)-9,9-dimethyl-9H-fluoren-3-yl)methanol (8)

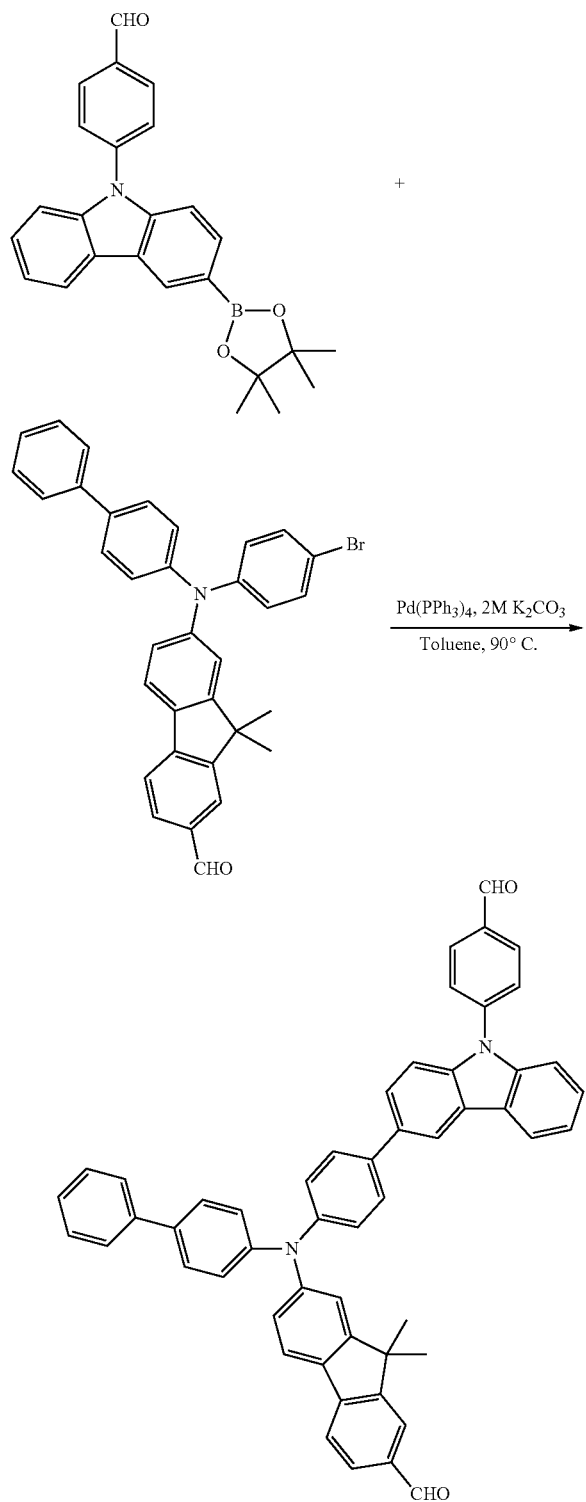

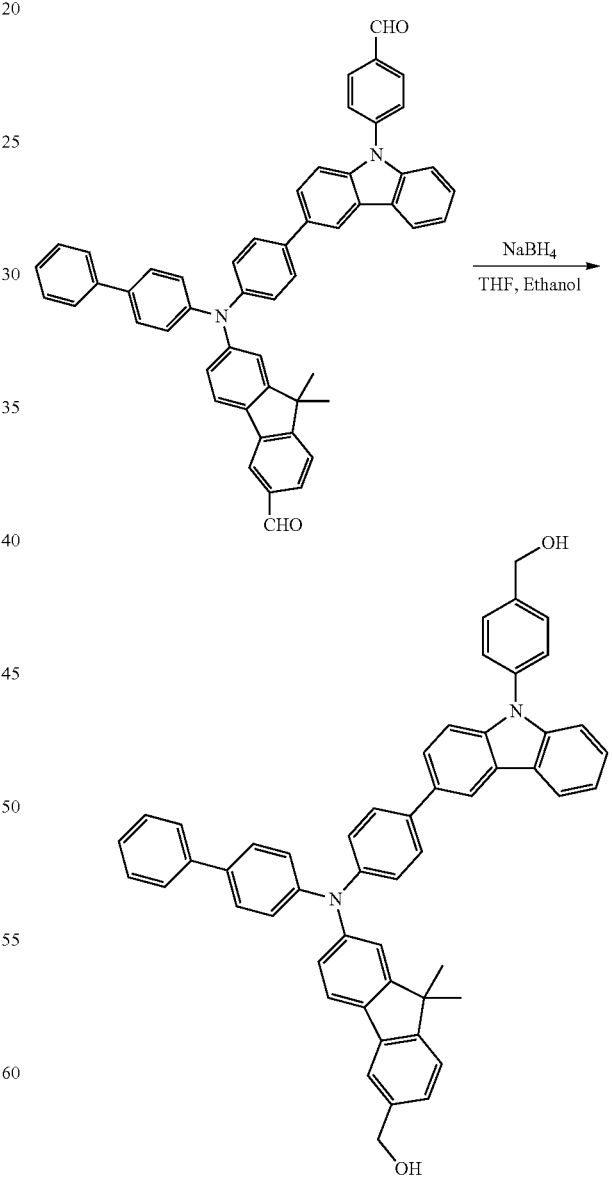

To a solution of 7 (734 mg, 1 mmol) in 10 mL THF and 10 mL ethanol at 40° C., NaBH$_4$ (302 mg, 8 mmol), was added under nitrogen atmosphere. The solution was allowed to stir at room temperature for 2 hours. Then, aqueous hydrochloric acid solution was added, until pH 5, and the mixture was kept stirring for 30 minutes. The solvent was removed under vacuum, and the residue was extracted with dichloromethane. The product was then dried under vacuum, and used for the next step without further purification. MS (ESI): 739.32 [M+H]⁺.

Synthesis of N-([1,1'-biphenyl]-4-yl)-6-((bicyclo [4.2.0]octa-1,3,5-trien-7-yloxy)methyl)-N-(4-(9-(4-((bicyclo[4.2.0]octa-1,3,5-trien-7-yloxy)methyl)phenyl)-9H-carbazol-3-yl)phenyl)-9,9-dimethyl-9H-fluoren-2-amine (9)

Scheme 9

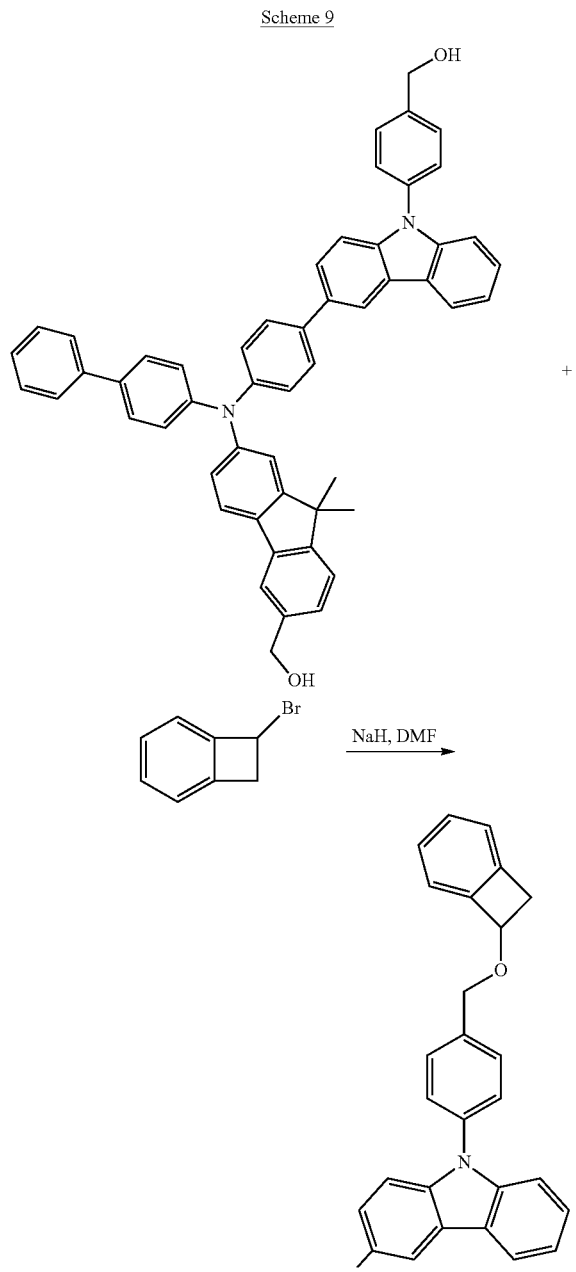

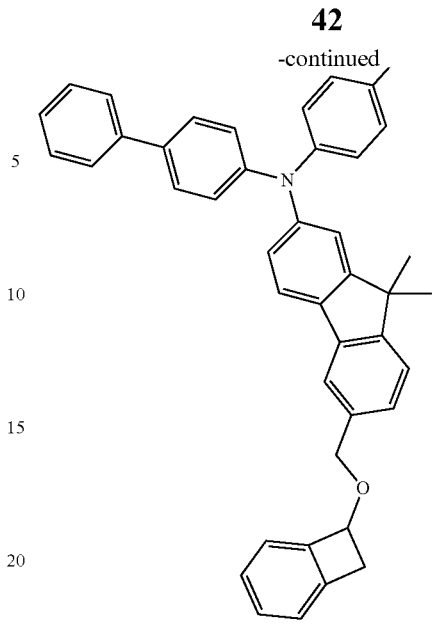

To a solution of 8 (3.69 g, 5 mmol, 738) in 50 mL dry DMF was added NaH (432 mg, 18 mmol, 24), then the mixture was stirred at room temperature for one hour. Then BCB-Br (2.75 g, 15 mmol, 183) was added to above solution via syringe. The mixture was heated to 60° C. for 24 hours. After quenched with water, the mixture was poured into water to remove DMF. The residue was filtrated, and the resulting solid was dissolved with dichloromethane, which was then washed with water. The solvent was removed under vacuum, and the residue was extracted with dichloromethane. The product was then obtained by column chromatography on silica gel with PE:EA (5:1) as the eluent. MS (ESI): 943.42 [M+H]⁺.

Synthesis of 3-bromo-9-(4-bromophenyl)-9H-carbazole (10)

Scheme 10

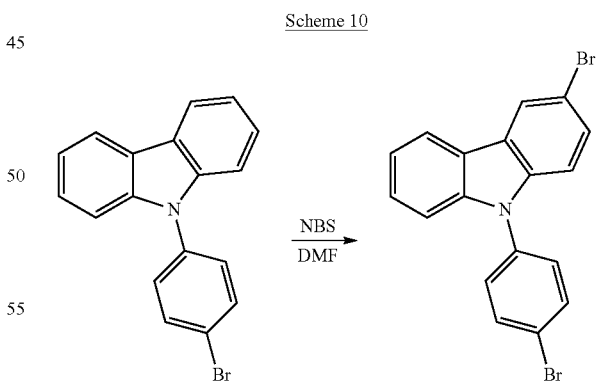

To a solution of 9 (4-bromophenyl)-9H-carbazole (32.2 g, 100 mmol) in 150 mL DMF, N-bromosuccinimide (NBS) (17.8 g, 100 mmol) in 100 mL DMF, was added dropwise in 30 minutes. After addition, the mixture was stirred at room temperature for 12 hours, and then poured into water to precipitate the product. The solid was filtrated, and recrystallized from dichloromethane and ethanol, to give white solid (yield: 92%). MS (ESI): 402.09 [M+H]⁺.

Synthesis of 9-(4-formylphenyl)-9H-carbazole-3-carbaldehyde (11)

Scheme 11

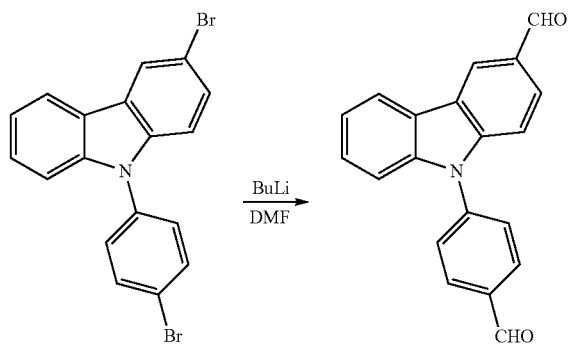

To a solution of 10 (8.02 g, 20 mmol) in THF (500 mL), n-BuLi (24 mL of a 2.5 M solution in hexanes, 60 mmol) was added at a rate to keep the internal temperature at −78° C. The mixture was stirred at −78° C. for one hour, and 10 mL DMF, with 10 mL THF, was added dropwise. After the addition, the reaction mixture was stirred at −45° C. for 30 minutes, and at 0° C. for an additional 30 minutes. Saturated aqueous NH4Cl (400 mL) was added. The layers were separated, and the aqueous layer was washed with a solution of ether:$CH_2Cl_2$ (2×100 m L, 9:1). The combined organic layers were washed with $H_2O$, saturated aqueous NaCl, dried over anhydrous MgSO4, and concentrated under reduced pressure. The residual was further purified through column chromatography to give crude product (yield: 65%). MS (ESI): 300.09 [M+H]+.

Synthesis of 6-bromo-9-(4-formylphenyl)-9H-carbazole-3-carbaldehyde (12)

Scheme 12

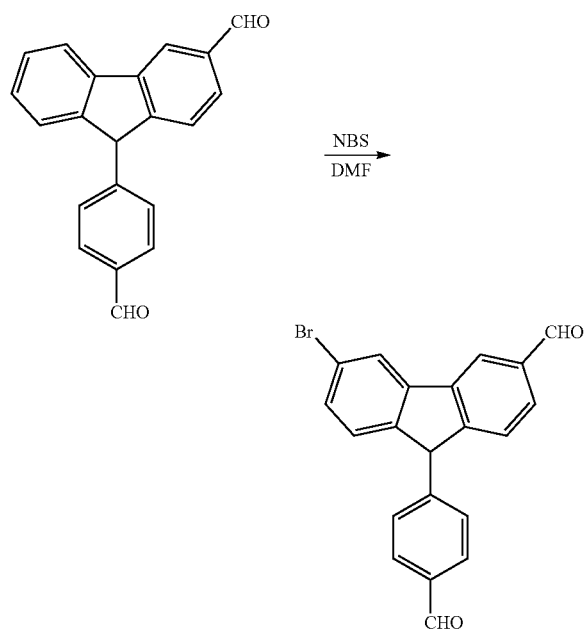

To a solution of 11 (0.898 g, 3 mmol, 1.00 equiv) in DCM (20 mL), NBS (0.587 mg, 3.3 mmol) was added. After stirred for 4 hours, the precipitate formed was filtered, and washed with ethanol to afford the product (yield: 84%). MS (ESI): 378.01 [M+H]+.

Synthesis of N-([1,1'-biphenyl]-4-yl)-9,9-dimethyl-N-(4-(4,4,5,5-tetramethyl-1,3,2-dioxaborolan-2-yl)phenyl)-9H-fluoren-2-amine (13)

Scheme 13

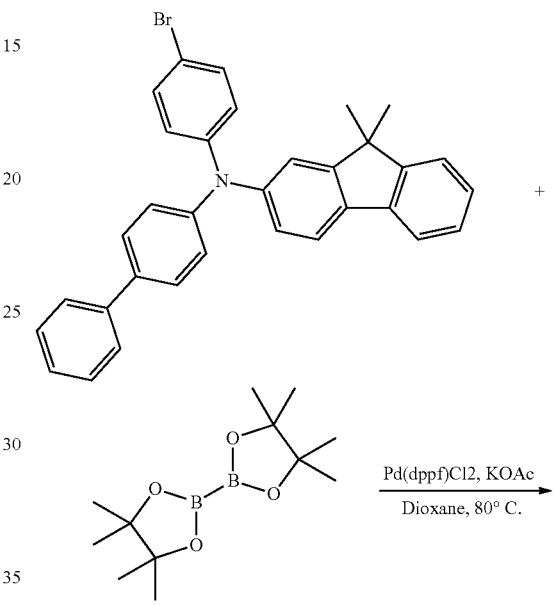

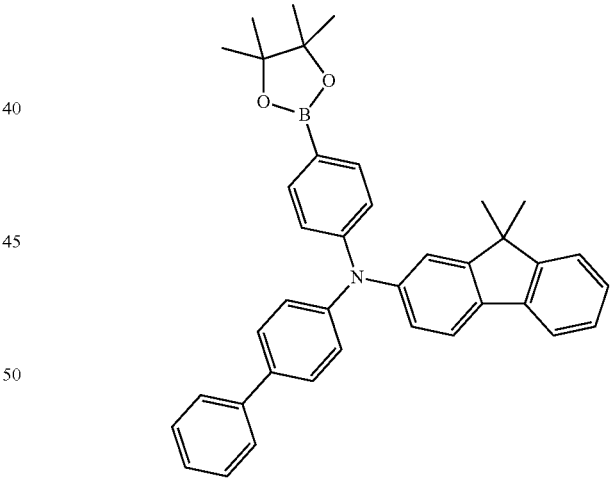

A mixture of 2 (15.48 g, 30 mmol), 4,4,4',4',5,5,5',5'-octamethyl-2,2'-bi(1,3,2-dioxaborolane) (9.14 g, 36 mmol), Pd(dppf)$_2$Cl$_2$ (571 mg, 0.75 mmol), CH$_3$COOK (4.41 g, 45 mmol), and 60 mL of dry dioxane, was heated at 85° C., under nitrogen atmosphere for 12 hours. After cooling to room temperature, the solvent was removed under vacuum, and then water was added. The mixture was extracted with CH$_2$Cl$_2$. The organic layer was collected, and dried over anhydrous sodium sulphate. After filtration, the filtrate was evaporated to remove solvent, and the residue was purified through column chromatography on silica gel to give white solid (yield: 84%). MS (ESI): 564.30[M+H]+.

Synthesis of 6-(4-([1,1'-biphenyl]-4-yl(9,9-dimethyl-9H-fluoren-2-yl)amino)phenyl)-9-(4-formylphenyl)-9H-carbazole-3-carbaldehyde (14)

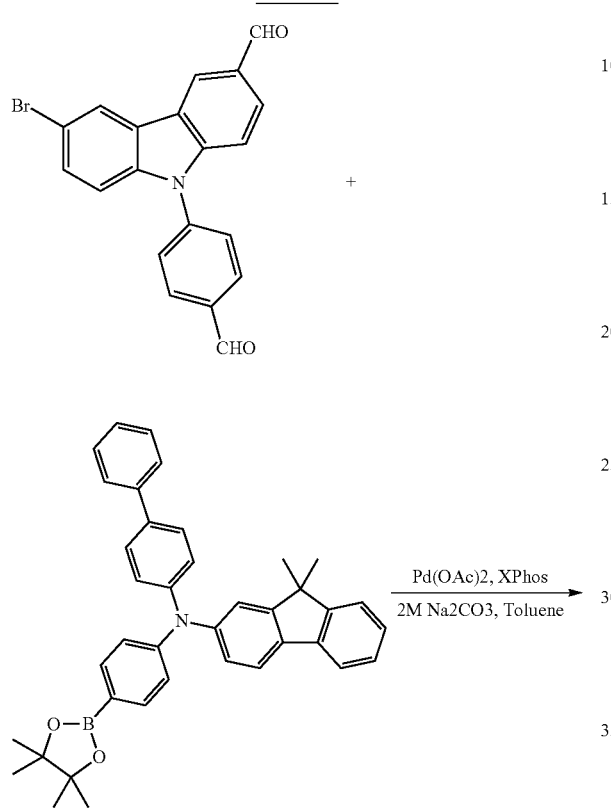

A mixture of 12 (0.756 g, 2 mmol), 13 (1.24 g, 2.2 mmol), Pd(OAc)₂ (12.8 mg, 0.06 mmol) and X-Phos (28.6 mg, 0.06 mmol), was added into 20 mL of a "1:1:2 mixture of aq. 2.0M Na₂CO₃:ethanol:toluene." The reaction mixture was stirred overnight, under an nitrogen atmosphere at 90° C., and then poured into EtOAc. The organics were washed with water and brine, and then dried over MgSO₄. The solvent was removed under reduced pressure, and the residue was purified through column chromatography on silica gel, to give yellow solid (yield: 64%). MS (ESI): 735.29 [M+H]+.

Synthesis of (4-(3-(4-([1,1'-biphenyl]-4-yl(9,9-dimethyl-9H-fluoren-2-yl)amino)phenyl)-6-(hydroxymethyl)-9H-carbazol-9-yl)phenyl)methanol (15)

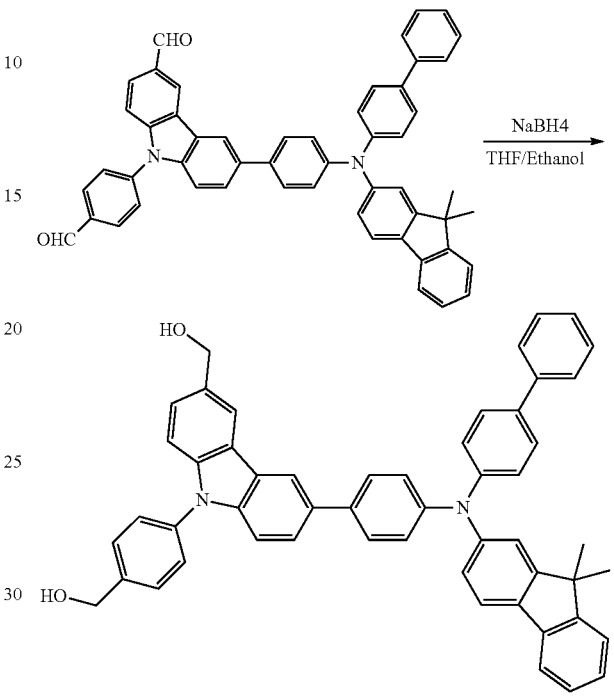

To a solution of 14 (734 mg, 1 mmol) in 10 mL THF and 10 mL ethanol, at 40° C., NaBH₄ (302 mg, 8 mmol) was added under nitrogen atmosphere. The solution was allowed to stir at room temperature for 2 hours. Then, aqueous hydrochloric acid solution was added, until pH 5, and the mixture was kept stirring for 30 minutes. The solvent was removed under vacuum, and the residue was extracted with dichloromethane. The product was then dried under vacuum, and used for the next step, without further purification. MS (ESI): 739.32 [M+H]⁺.

Synthesis of N-([1,1'-biphenyl]-4-yl)-N-(4-(6-((bicyclo[4.2.0]octa-1(6),2,4-trien-7-yloxy)methyl)-9-(4-((bicyclo[4.2.0]octa-1(6),2,4-trien-7-yloxy)methyl)phenyl)-9H-carbazol-3-yl)phenyl)-9,9-dimethyl-9H-fluoren-2-amine (16)

Scheme 16

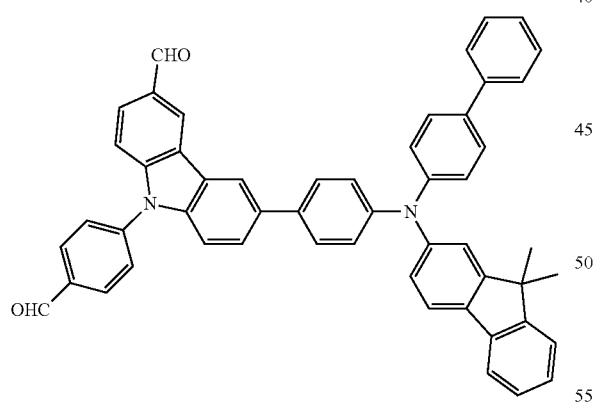

-continued

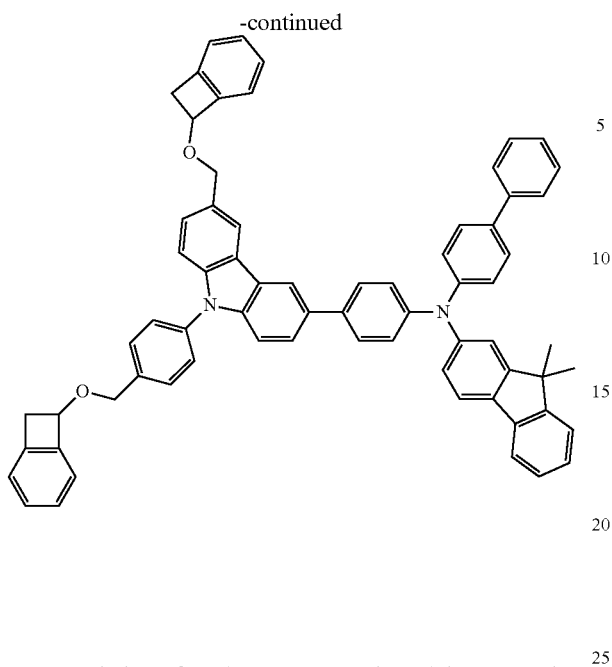

To a solution of 15 (3.69 g, 5 mmol, 738) in 50 mL dry DMF, was added NaH (432 mg, 18 mmol), then the mixture was stirred at room temperature for one hour. Next, BCB-Br (2.75 g, 15 mmol) was added to above solution via syringe. The mixture was heated to 60° C. for 24 hours. After being quenched with water, the mixture was poured into water to remove DMF. The residue was filtered, and the resulting solid was dissolved with dichloromethane, which was then washed with water. The solvent was removed under vacuum, and the residue was extracted with dichloromethane. The product was then obtained by column chromatography on silica gel with PE:EA (5:1) as the eluent. MS (ESI): 943.42 [M+H]$^+$.

The inventive compositions can be used to form hole-transporting materials for use in electroluminescent devices. For example, an inventive composition can be used to form a "light emitting device as follows. An indium tin oxide (ITO) glass substrate (2*2 cm) can be cleaned, and then treated with a UV Ozone cleaner for 15 minutes. The hole injection layer (HIL) material can be spin-coated, from a water solution, onto the ITO substrates, in a glovebox (for example, Argon atmosphere), and annealed at 150° C. for 20 minutes. The substrate can be transferred into a thermal evaporator for the deposition of an HTL layer. For an inventive composition (HTL), the composition can be deposited from anisole solution, and annealed at 150° C. for 10 minutes, to remove organic solvent. After that, the crosslinking of polymeric HTL can be carried out on a hotplate, in a glovebox, at 205° C. for 10 minutes. Then an emitting layer (EML), an electron transfer layer (ETL), and a cathode can be sequentially deposited. Finally the device can be hermetically sealed, prior to testing.

The invention claimed is:

1. A composition comprising at least one compound selected from Structure A:

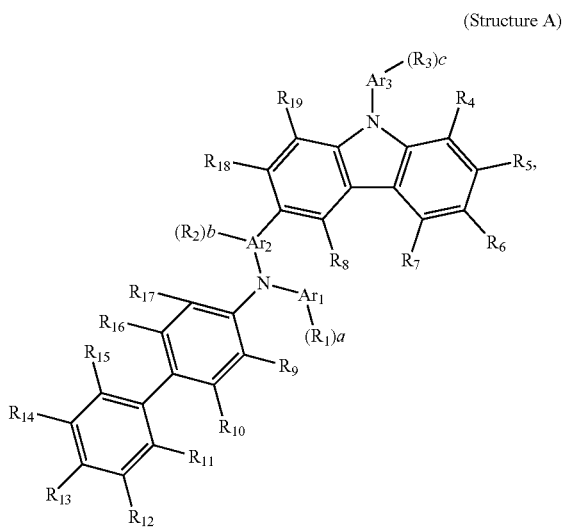

(Structure A)

wherein groups $R_4$ to $R_{19}$ are each, independently, selected from hydrogen, a hydrocarbon, a substituted hydrocarbon, a halogen, a cyano, a nitro, an alkoxy, or a hydroxyl;

$Ar_1$ is selected from a substituted aryl, an unsubstituted aryl, a substituted heteroaryl, or an unsubstituted heteroaryl;

$(R_1)a$ is selected from hydrogen, a hydrocarbon, a substituted hydrocarbon, a halogen, a cyano, a nitro, an alkoxy, or a hydroxyl;

$Ar_2$ is selected from a substituted aryl, an unsubstituted aryl, a substituted heteroaryl, or an unsubstituted heteroaryl;

$(R_2)b$ is selected from hydrogen, a hydrocarbon, a substituted hydrocarbon, a halogen, a cyano, a nitro, an alkoxy, or a hydroxyl;

$Ar_3$ is selected from a substituted aryl, an unsubstituted aryl, a substituted heteroaryl, or an unsubstituted heteroaryl;

$(R_3)c$ is selected from hydrogen, a hydrocarbon, a substituted hydrocarbon, a halogen, a cyano, a nitro, an alkoxy, or a hydroxyl; and with the proviso that at least one of groups $(R_1)a$, $(R_2)b$, $(R_3)c$ or $R_4$ to $R_{19}$ is independently selected from the benzocyclobutene structures of Structure B, Structure C, Structure D, or Structure E, as follows:

B)

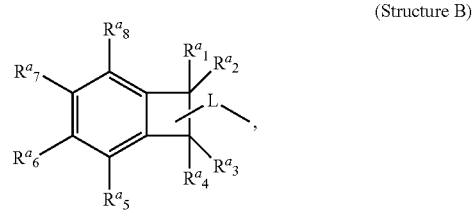

(Structure B)

wherein Structure B is connected to Structure A though -L-;

wherein, for Structure B:

1b) one of $R^a_1$, $R^a_2$, $R^a_3$ or $R^a_4$ is -L-; and wherein -L- is selected from the following: —O—; -alkylene-; —O-alkylene-; —O-arylene-; —O-alkylene-arylene-; —O-alkylene-O—; —O-alkylene-O-alkylene-O—; —O-arylene-O—; —O-alkylene-arylene-O—; —O—(CH2CH2-O)n-, wherein n is from 2 to 20; —O-alkylene-O-alkylene-; —O-alkylene-O-arylene-; —O-arylene-O—; —O-arylene-O-alkyene-; —O-arylene-O-arylene-; or a covalent bond linking 'Structure B" to "Structure A"; and 2b) the remaining $R^a_1$, $R^a_2$, $R^a_3$ and $R^a_4$ are each, independently, selected from hydrogen, a hydrocarbon, a substituted hydrocarbon, a halogen, a cyano, a nitro, an alkoxy, or a hydroxyl; and 3b) $R^a_5$, $R^a_6$, $R^a_7$ or $R^a_8$ are each, independently, selected from hydrogen, a hydrocarbon, a substituted hydrocarbon, a halogen, a cyano, a nitro, an alkoxy, or a hydroxyl;

C)

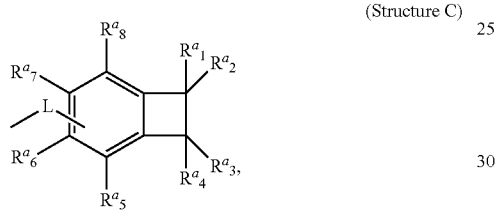

(Structure C)

wherein Structure C is connected to Structure A though -L-;

wherein, for Structure C:

1c) one of $R^a_5$, $R^a_6$, $R^a_7$ or $R^a_8$ is -L-; and wherein -L- is selected from the following: —O—; -alkylene-; -arylene-; —O-alkylene-; —O-arylene-; —O-alkylene-arylene-; —O-alkylene-O—; —O-alkylene-O-alkylene-O—; —O-arylene-O—; —O-alkylene-arylene-O—; —O—(CH2CH2-O)n-, wherein n is from 2 to 20; —O-alkylene-O-alkylene-; —O-alkylene-O-arylene-; —O-arylene-O-alkyene-; —O-arylene-O-arylene-; or a covalent bond linking 'Structure C" to "Structure A";

2c) the remaining $R^a_5$, $R^a_6$, $R^a_7$ or $R^a_8$ are each, independently, selected from hydrogen, a hydrocarbon, a substituted hydrocarbon, a halogen, a cyano, a nitro, or a hydroxyl;

3c) $R^a_1$, $R^a_2$, $R^a_3$ and $R^a_4$ are each, independently, selected from hydrogen, a hydrocarbon, a substituted hydrocarbon, a halogen, a cyano, a nitro, an alkoxy, or a hydroxyl;

D)

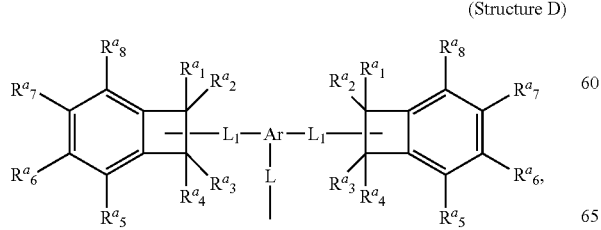

(Structure D)

wherein Structure D is connected to Structure A though -L-;

wherein, for Structure D:

1di) for one $-L_1-$, one of $R^a_1$, $R^a_2$, $R^a_3$ or $R^a_4$ of the benzocyclobutene moiety directly bonded to this $-L_1-$, is independently $-L_1-$; and wherein $-L_1-$ is selected from the following: —O—; -alkylene-; —O-alkylene-; —O-arylene-; —O-alkylene-arylene-; —O-alkylene-O—; —O-alkylene-O-alkylene-O—; —O-arylene-O—; —O-alkylene-arylene-O—; —O—(CH2CH2-O)n-, wherein n is from 2 to 20; —O-alkylene-O-alkylene-; —O-alkylene-O-arylene-; —O-arylene-O—; —O-arylene-O-alkyene-; —O-arylene-O-arylene-; —O-alkylene-arylene-O—; or a covalent bond linking the 4 carbon ring to Ar;

1dii) for the other $-L_1-$, one of $R^a_1$, $R^a_2$, $R^a_3$ or $R^a_4$ of the other benzocyclo-butene moiety directly bonded to this $-L_1-$, is independently $-L_1-$; and wherein $-L_1-$ is selected from the following: —O—; -alkylene-; —O-alkylene-; —O-arylene-; —O-alkylene-arylene-; —O-alkylene-O—; —O-alkylene-O-alkylene-O—; —O-arylene-O—; —O— alkylene-arylene-O—; —O—(CH2CH2-O)n-, wherein n is from 2 to 20; —O-alkylene-O-alkylene-; —O-alkylene-O-arylene-; —O-arylene-O—; —O-arylene-O-alkyene-; —O-arylene-O-arylene-; —O-alkylene-arylene-O—; or a covalent bond linking the 4 carbon ring to Ar;

2d) Ar is a substituted or unsubstituted C5-C60 aryl group;

3d) -L- is selected from the following: —O—; -alkylene-; -arylene-; —O-alkylene-; —O-arylene-; —O-alkylene-arylene-; —O-alkylene-O—; —O-alkylene-O-alkylene-O—; —O-arylene-O—; —O-alkylene-arylene-O—; —O—(CH2CH2-O)n-, wherein n is from 2 to 20; —O-alkylene-O-alkylene-; —O-alkylene-O-arylene-; —O-arylene-O—; —O-arylene-O-alkyene-; —O-arylene-O-arylene-; or a covalent bond linking "Structure D" to "Structure A";

4di) the remaining $R^a_1$, $R^a_2$, $R^a_3$ and $R^a_4$ of one benzocyclobutene moiety are each, independently, selected from hydrogen, a hydrocarbon, a substituted hydrocarbon, a halogen, a cyano, a nitro, or a hydroxyl;

4dii) the remaining $R^a_1$, $R^a_2$, $R^a_3$ and $R^a_4$ of the other benzocyclobutene moiety are each, independently, selected from hydrogen, a hydrocarbon, a substituted hydrocarbon, a halogen, a cyano, a nitro, or a hydroxyl;

5di) $R^a_5$, $R^a_6$, $R^a_7$ or $R^a_8$ of one benzocyclobutene moiety are each, independently, selected from hydrogen, a hydrocarbon, a substituted hydrocarbon, a halogen, a cyano, a nitro, or a hydroxyl;

5dii) $R^a_5$, $R^a_6$, $R^a_7$ or $R^a_8$ of the other benzocyclobutene moiety are each, independently, selected from hydrogen, a hydrocarbon, a substituted hydrocarbon, a halogen, a cyano, a nitro, or a hydroxyl;

E)

(Structure E)

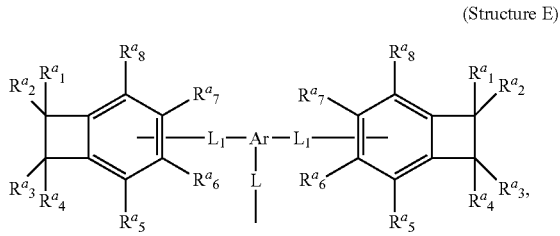

wherein

Structure E is connected to Structure A though -L-; wherein, for Structure E:

1ei) for one -$L_1$-, one of $R^a_5$, $R^a_6$, $R^a_7$ or $R^a_8$ of the benzocyclobutene moiety directly bonded to this -$L_1$-, is independently -$L_1$-; and wherein -$L_1$- is selected from the following: —O—; -alkylene-; -arylene-; —O-alkylene-; —O-arylene-; —O-alkylene-arylene-; —O-alkylene-O—; —O-alkylene-O-alkylene-O—; —O-arylene-O—; —O-alkylene-arylene-O—; —O—(CH2CH2-O)n-, wherein n is from 2 to 20; —O-alkylene-O-alkylene-; —O-alkylene-O-arylene-; —O-arylene-O—; —O-arylene-O-alkyene-; —O-arylene-O-arylene-; or a covalent bond linking the 6-carbon ring to Ar;

1eii) for the other -$L_1$-, one of $R^a_5$, $R^a_6$, $R^a_7$ or $R^a_8$ of the other benzocyclo-butene moiety directly bonded to this -$L_1$-, is independently -$L_1$-; and wherein -$L_1$- is selected from the following: —O—; -alkylene-; -arylene-; —O-alkylene-; —O-arylene-; —O-alkylene-arylene-; —O-alkylene-O—; —O-alkylene-O-alkylene-O—; —O-arylene-O—; —O— alkylene-arylene-O—; —O—(CH2CH2-O)n-, wherein n is from 2 to 20; —O-alkylene-O-alkylene-; —O-alkylene-O-arylene-; —O-arylene-O—; —O-arylene-O-alkyene-; —O-arylene-O-arylene-; or a covalent bond linking the 6-carbon ring to Ar;

2e) Ar is a substituted or unsubstituted C5-C60 aryl group; and

3e) -L- is selected from the following: —O—; -alkylene-; -arylene-; —O-alkylene-; —O-arylene-; —O-alkylene-arylene-; —O-alkylene-O—; —O-alkylene-O-alkylene-O—; —O-arylene-O—; —O-alkylene-arylene-O—; —O—(CH2CH2-O)n-, wherein n is from 2 to 20; —O-alkylene-O-alkylene-; —O-alkylene-O-arylene-; —O-arylene-O—; —O-arylene-O-alkyene-; —O-arylene-O-arylene-; or a covalent bond linking "Structure E" to "Structure A";

4ei) the remaining $R^a_5$, $R^a_6$, $R^a_7$ or $R^a_8$ of one benzocyclobutene moiety are each, independently, selected from hydrogen, a hydrocarbon, a substituted hydrocarbon, a halogen, a cyano, a nitro, or a hydroxyl;

4eii) the remaining $R^a_5$, $R^a_6$, $R^a_7$ or $R^a_8$ of the other benzocyclobutene moiety are each, independently, selected from hydrogen, a hydrocarbon, a substituted hydrocarbon, a halogen, a cyano, a nitro, or a hydroxyl;

5ei) $R^a_1$, $R^a_2$, $R^a_3$ and $R^a_4$ of one benzocyclobutene moiety are each, independently, selected from hydrogen, a hydrocarbon, a substituted hydrocarbon, a halogen, a cyano, a nitro, an alkoxy, or a hydroxyl;

5eii) $R^a_1$, $R^a_2$, $R^a_3$ and $R^a_4$ of the other benzocyclobutene moiety are each, independently, selected from hydrogen, a hydrocarbon, a substituted hydrocarbon, a halogen, a cyano, a nitro, an alkoxy, or a hydroxyl; and wherein for Structure A, two or more R groups may optionally form one or more ring structures; and wherein for Structure A, one or more hydrogen atoms may be optionally substituted with deuterium.

2. The composition of claim 1, wherein Structure A is selected from Structure A-I as follows:

(Structure A-I)

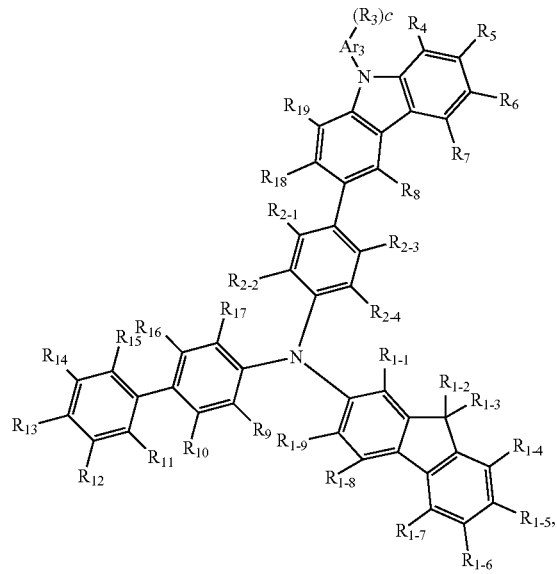

wherein $R_{2-1}$, $R_{2-2}$, $R_{2-3}$ and $R_{2-4}$ are each independently selected from the following: hydrogen, a hydrocarbon, a substituted hydrocarbon, a halogen, a cyano, a nitro, an alkoxy, or a hydroxyl; and wherein one of $R_{2-1}$, $R_{2-2}$, $R_{2-3}$ or $R_{2-4}$ is ($R_2$)b; and wherein $R_{1-1}$, $R_{1-4}$, $R_{1-5}$, $R_{1-6}$, $R_{1-7}$, $R_{1-8}$ and $R_{1-9}$ are each independently selected from the following: hydrogen, a hydrocarbon, a substituted hydrocarbon, a halogen, a cyano, a nitro, an alkoxy, or a hydroxyl; and wherein one of $R_{1-1}$, $R_{1-4}$, $R_{1-5}$, $R_{1-6}$, $R_{1-7}$, $R_{1-8}$ or $R_{1-9}$ is ($R_1$)a; and wherein $R_{1-2}$ and $R_{1-3}$ are each independently selected from the following: hydrogen, a hydrocarbon, a substituted hydrocarbon, or a halogen; and wherein groups $R_4$ to $R_{19}$ are each, independently, selected from hydrogen, a hydrocarbon, a substituted hydrocarbon, a halogen, a cyano, a nitro, an alkoxy, or a hydroxyl;

$Ar_3$ is selected from a substituted aryl, an unsubstituted aryl, a substituted heteroaryl, or an unsubstituted heteroaryl;

($R_3$)c is selected from hydrogen, a hydrocarbon, a substituted hydrocarbon, a halogen, a cyano, a nitro, an alkoxy, or a hydroxyl; and with the proviso that at least one of groups ($R_1$)a, ($R_2$)b, ($R_3$)c or $R_4$ to $R_{19}$ is independently selected from Structure B, Structure C, or Structure D, or Structure E; and wherein for Structure A-I, two or more R groups may optionally form one or more ring structures; and wherein for Structure A-I, one or more hydrogen atoms may be optionally substituted with deuterium.

3. The composition of claim 1, wherein Structure A is selected from Structure A-II as follows:

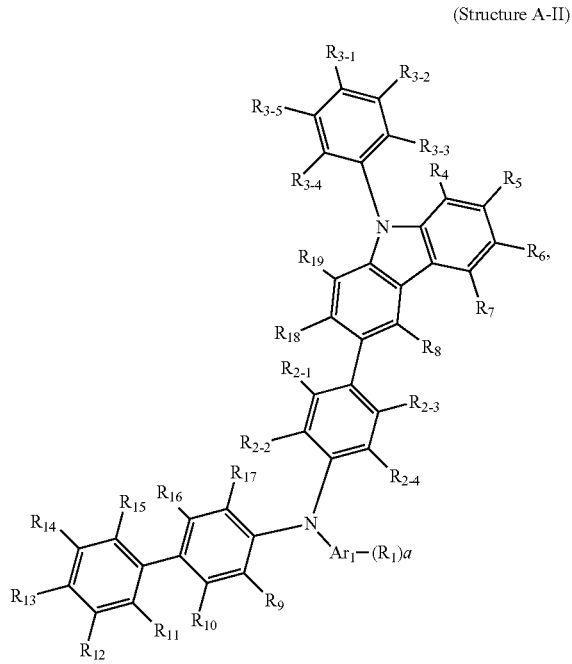

(Structure A-II)

wherein $R_{2-1}$, $R_{2-2}$, $R_{2-3}$ and $R_{2-4}$ are each independently selected from the following: hydrogen, a hydrocarbon, a substituted hydrocarbon, a halogen, a cyano, a nitro, an alkoxy, or a hydroxyl; and wherein one of $R_{2-1}$, $R_{2-2}$, $R_{2-3}$ and $R_{2-4}$ is $(R_2)b$; and wherein $R_{3-1}$, $R_{3-2}$, $R_{3-3}$, $R_{3-4}$ and $R_{3-5}$ are each independently selected from the following: hydrogen, a hydrocarbon, a substituted hydrocarbon, a halogen, a cyano, a nitro, an alkoxy, or a hydroxyl; and wherein one of $R_{3-1}$, $R_{3-2}$, $R_{3-3}$, $R_{3-4}$ or $R_{3-5}$ is $(R_3)c$; and wherein groups $R_4$ to $R_{19}$ are each, independently, selected from hydrogen, a hydrocarbon, a substituted hydrocarbon, a halogen, a cyano, a nitro, an alkoxy, or a hydroxyl;

$Ar_1$ is selected from a substituted aryl, an unsubstituted aryl, a substituted heteroaryl, or an unsubstituted heteroaryl;

$(R_1)a$ is selected from hydrogen, a hydrocarbon, a substituted hydrocarbon, a halogen, a cyano, a nitro, an alkoxy, or a hydroxyl; and with the proviso that at least one of groups $(R_1)a$, $(R_2)b$, $(R_3)c$ or $R_4$ to $R_{19}$ is independently selected from Structure B, Structure C, or Structure D, or Structure E; and wherein for Structure A-II, two or more R groups may optionally form one or more ring structures; and wherein for Structure A-II, one or more hydrogen atoms may be optionally substituted with deuterium.

4. The composition of claim 1, wherein Structure A is selected from Structure A-III as follows:

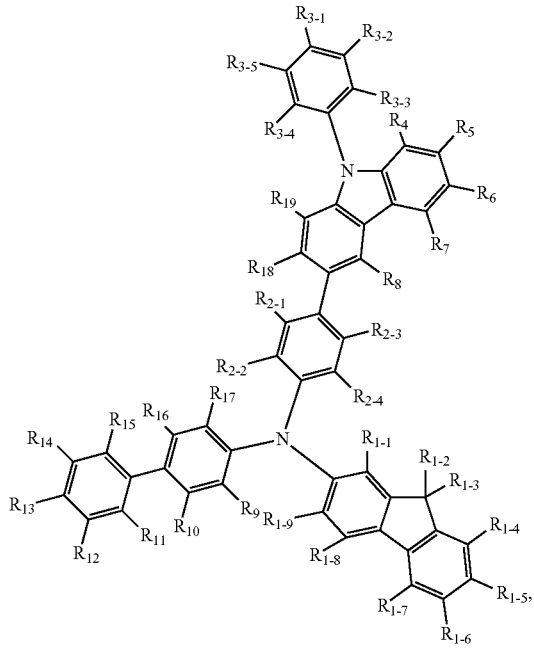

(Structure A-III)

wherein $R_{2-1}$, $R_{2-2}$, $R_{2-3}$ and $R_{2-4}$ are each independently selected from the following: hydrogen, a hydrocarbon, a substituted hydrocarbon, a halogen, a cyano, a nitro, an alkoxy, or a hydroxyl; and wherein one of $R_{2-1}$, $R_{2-2}$, $R_{2-3}$ and $R_{2-4}$ is $(R_2)b$; and wherein $R_{1-1}$, $R_{1-4}$, $R_{1-5}$, $R_{1-6}$, $R_{1-7}$, $R_{1-8}$ and $R_{1-9}$ are each independently selected from the following: hydrogen, a hydrocarbon, a substituted hydrocarbon, a halogen, a cyano, a nitro, an alkoxy, or a hydroxyl; and wherein one of $R_{1-1}$, $R_{1-4}$, $R_{1-5}$, $R_{1-6}$, $R_{1-7}$, $R_{1-8}$ or $R_{1-9}$ is $(R_1)a$; and wherein $R_{1-2}$ and $R_{1-3}$ are each independently selected from the following: hydrogen, a hydrocarbon, a substituted hydrocarbon, or a halogen; and wherein $R_{3-1}$, $R_{3-2}$, $R_{3-3}$, $R_{3-4}$ and $R_{3-5}$ are each independently selected from the following: hydrogen, a hydrocarbon, a substituted hydrocarbon, a halogen, a cyano, a nitro, an alkoxy, or a hydroxyl; and wherein one of $R_{3-1}$, $R_{3-2}$, $R_{3-3}$, $R_{3-4}$ or $R_{3-5}$ is $(R_3)c$; and wherein groups $R_4$ to $R_{19}$ are each, independently, selected from hydrogen, a hydrocarbon, a substituted hydrocarbon, a halogen, a cyano, a nitro, an alkoxy, or a hydroxyl;

with the proviso that at least one of groups $(R_1)a$, $(R_2)b$, $(R_3)c$ or $R_4$ to $R_{19}$ is independently selected from Structure B, Structure C, or Structure D, or Structure E; and wherein for Structure A-III, two or more R groups may optionally form one or more ring structures; and wherein for Structure A-III, one or more hydrogen atoms may be optionally substituted with deuterium.

5. The composition of claim 1, wherein, for Structure B, -L- is selected from the following: —O—, -alkylene-, —O-alkylene-, —O-phenylene-, —O-alkylene-phenylene-, or a covalent bond linking 'Structure B" to "Structure A".

6. The composition of claim 1, wherein, for Structure C, -L- is selected from the following: —O—, -alkylene-, —O- alkylene-, —O— phenylene-, —O-alkylene-phenylene-, or a covalent bond linking "Structure C" to "Structure A".

7. The composition of claim 1, wherein Structure B is selected from the following structures (i) or (ii):

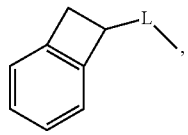
(i)

or

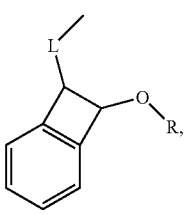
(ii)

wherein R is hydrogen, a hydrocarbon or a substituted hydrocarbon.

8. The composition of claim 1, wherein Structure C is selected from the following structures (iii) or (iv):

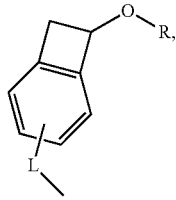
(iii)

wherein R is hydrogen, a hydrocarbon or a substituted hydrocarbon;

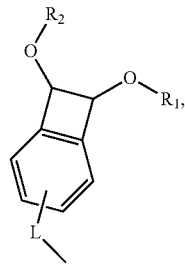
(iv)

wherein $R_1$ is hydrogen, a hydrocarbon or a substituted hydrocarbon; and $R_2$ is hydrogen, a hydrocarbon or a substituted hydrocarbon.

9. The composition of claim 1, wherein Structure D is selected from the following structure (v):

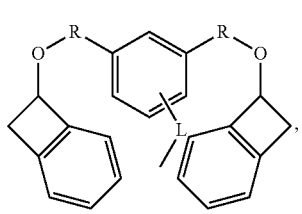
(v)

wherein each R is independently hydrogen, a hydrocarbon or a substituted hydrocarbon.

10. The composition of claim 1, wherein for Structure A, R9-R12 and R14-R17 are each hydrogen.

11. The composition of claim 1, wherein Structure A is selected from the following structures (a) through (r):

a

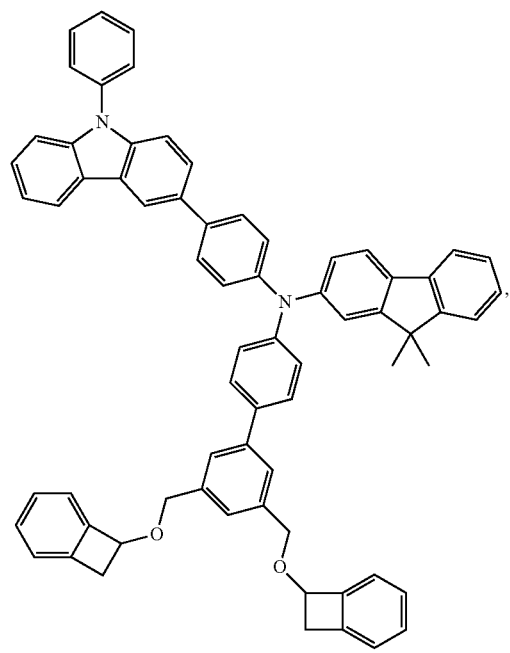

-continued
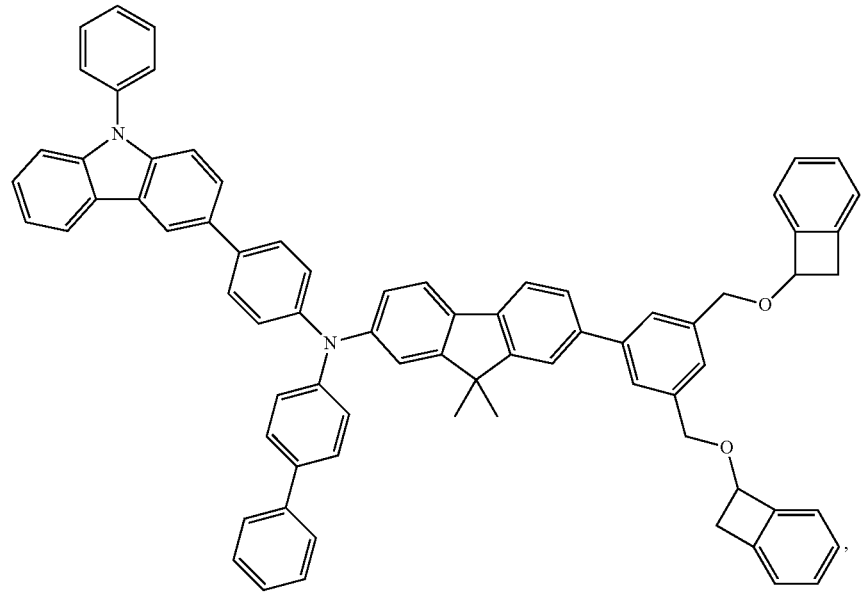
b
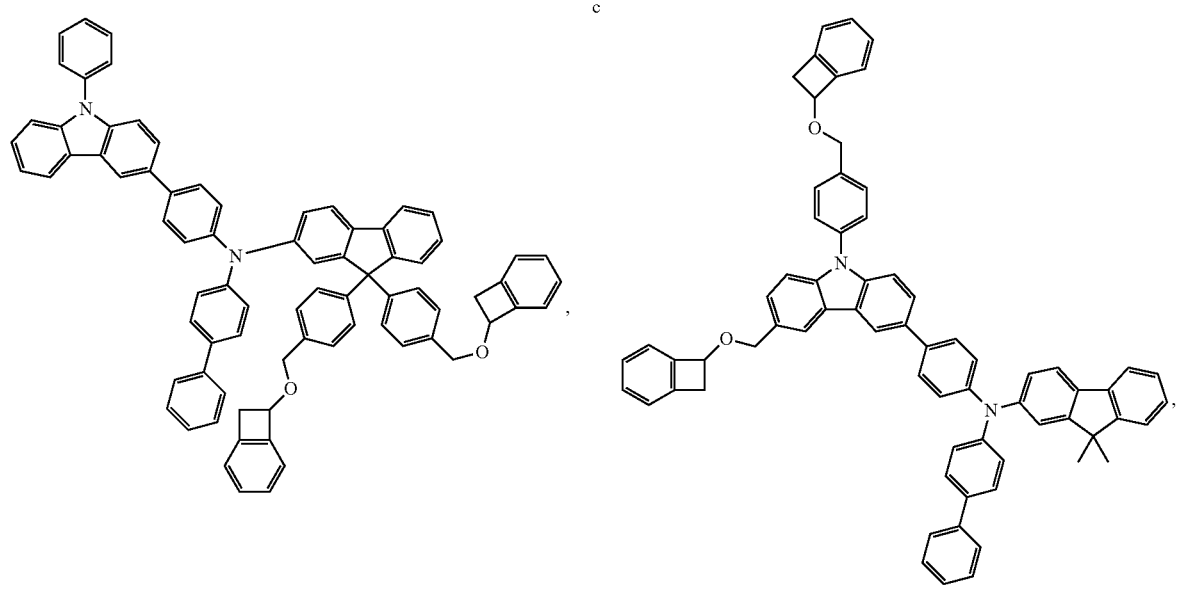
c
d

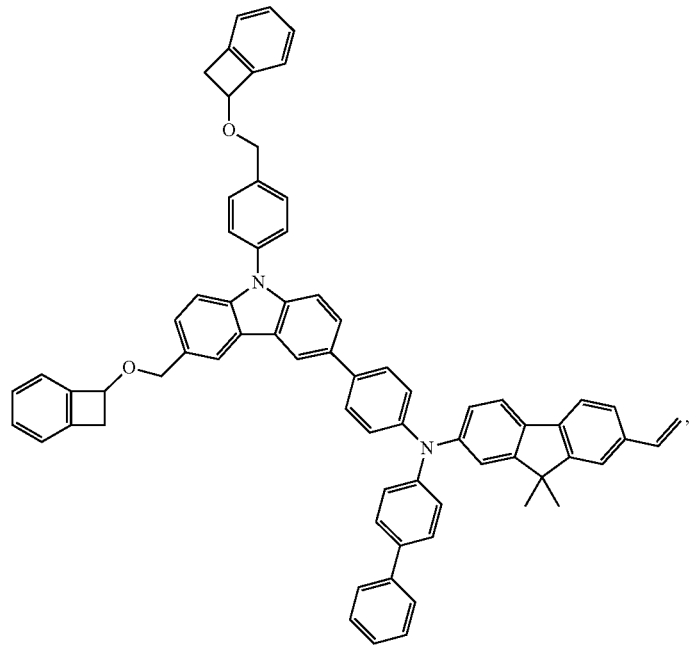
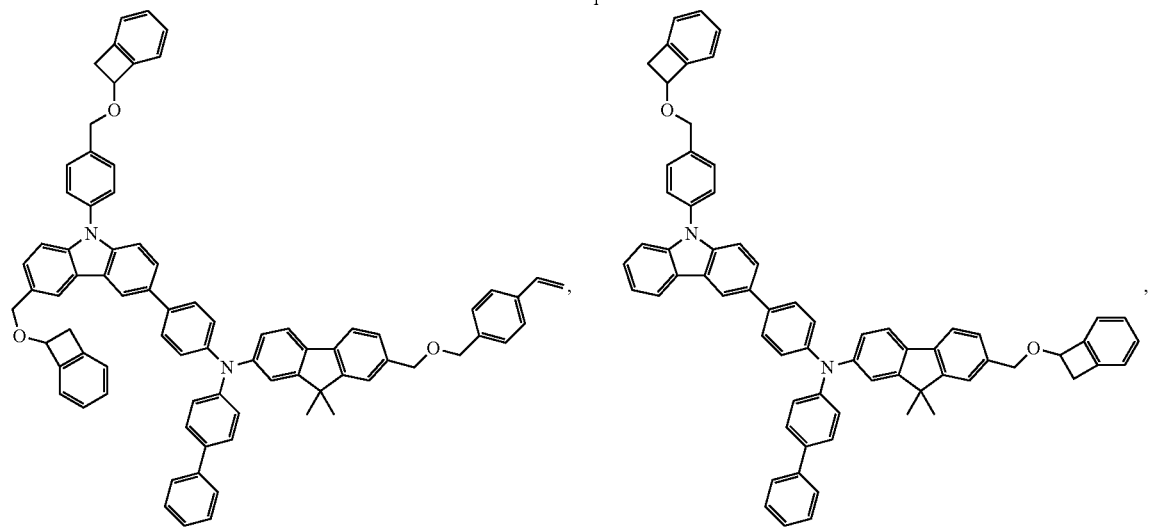

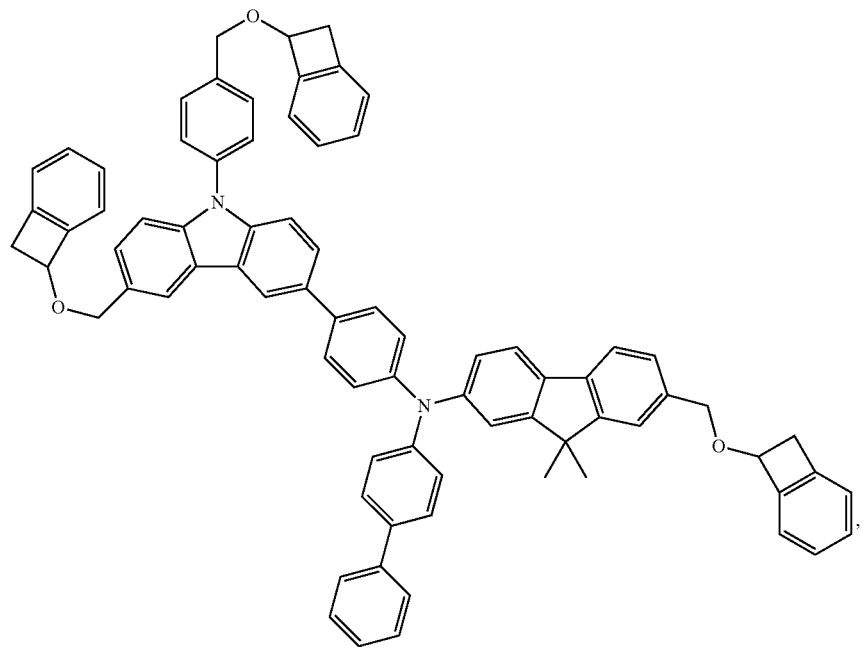
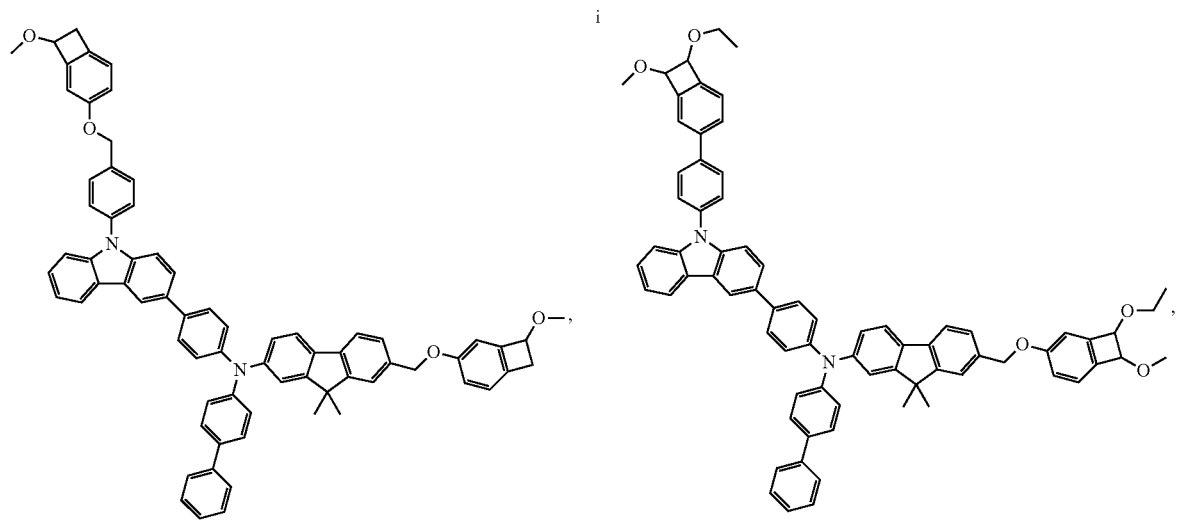

-continued
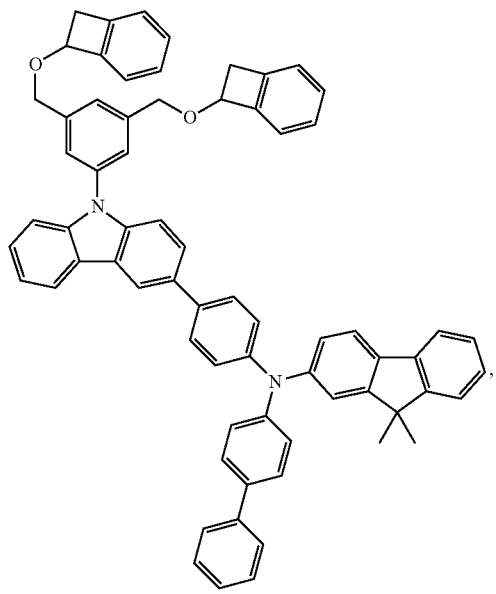
k
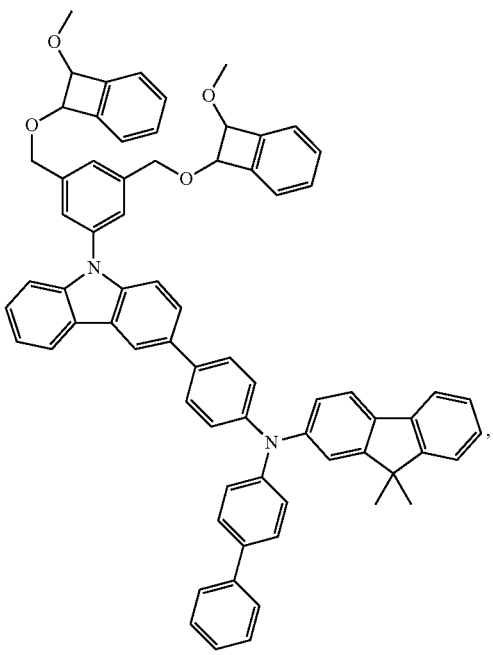
l
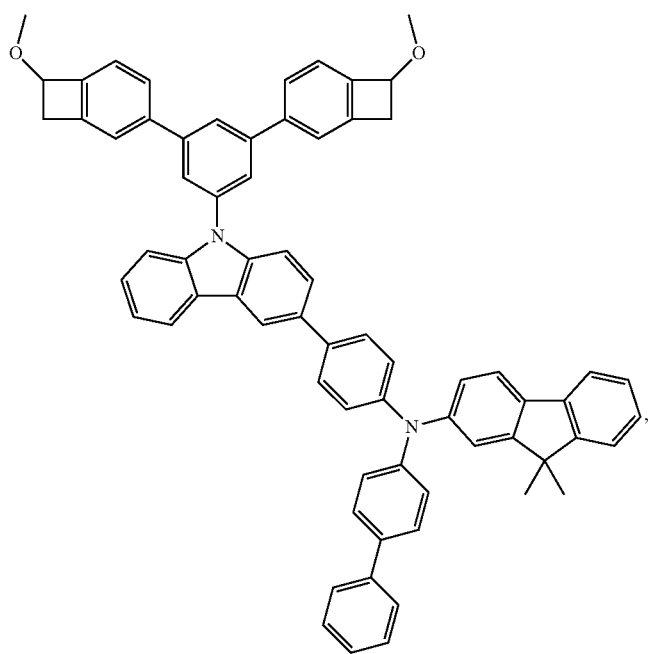
m

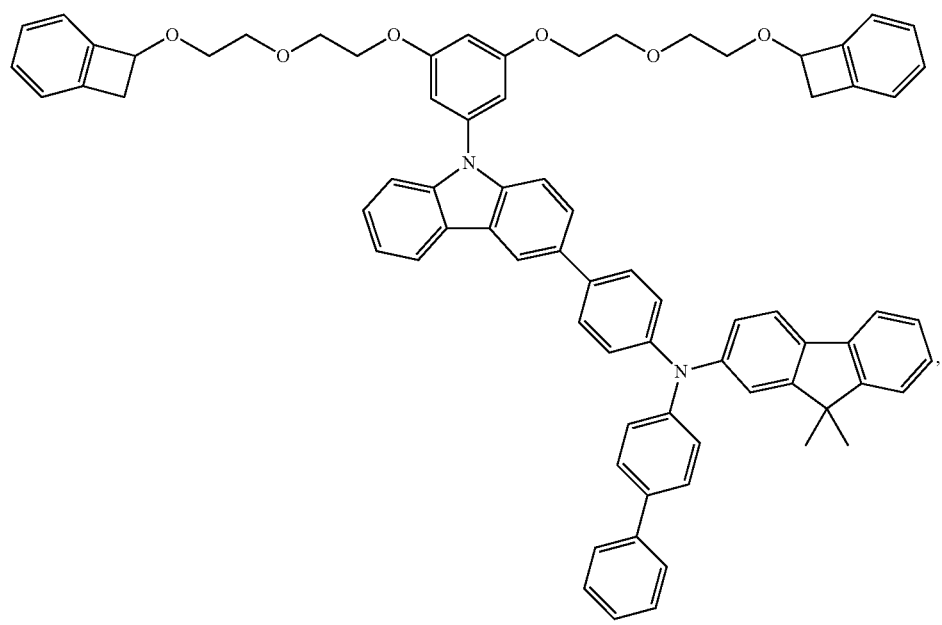
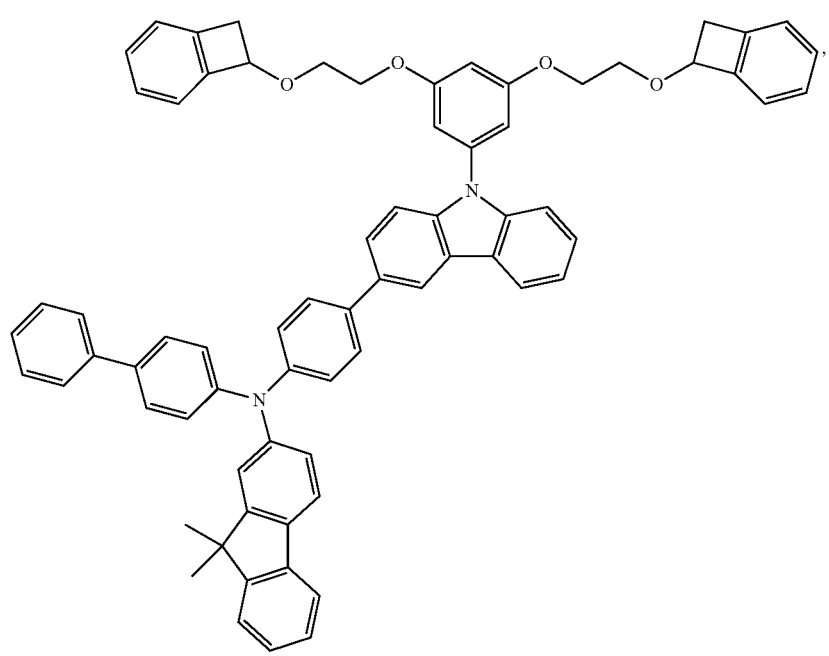

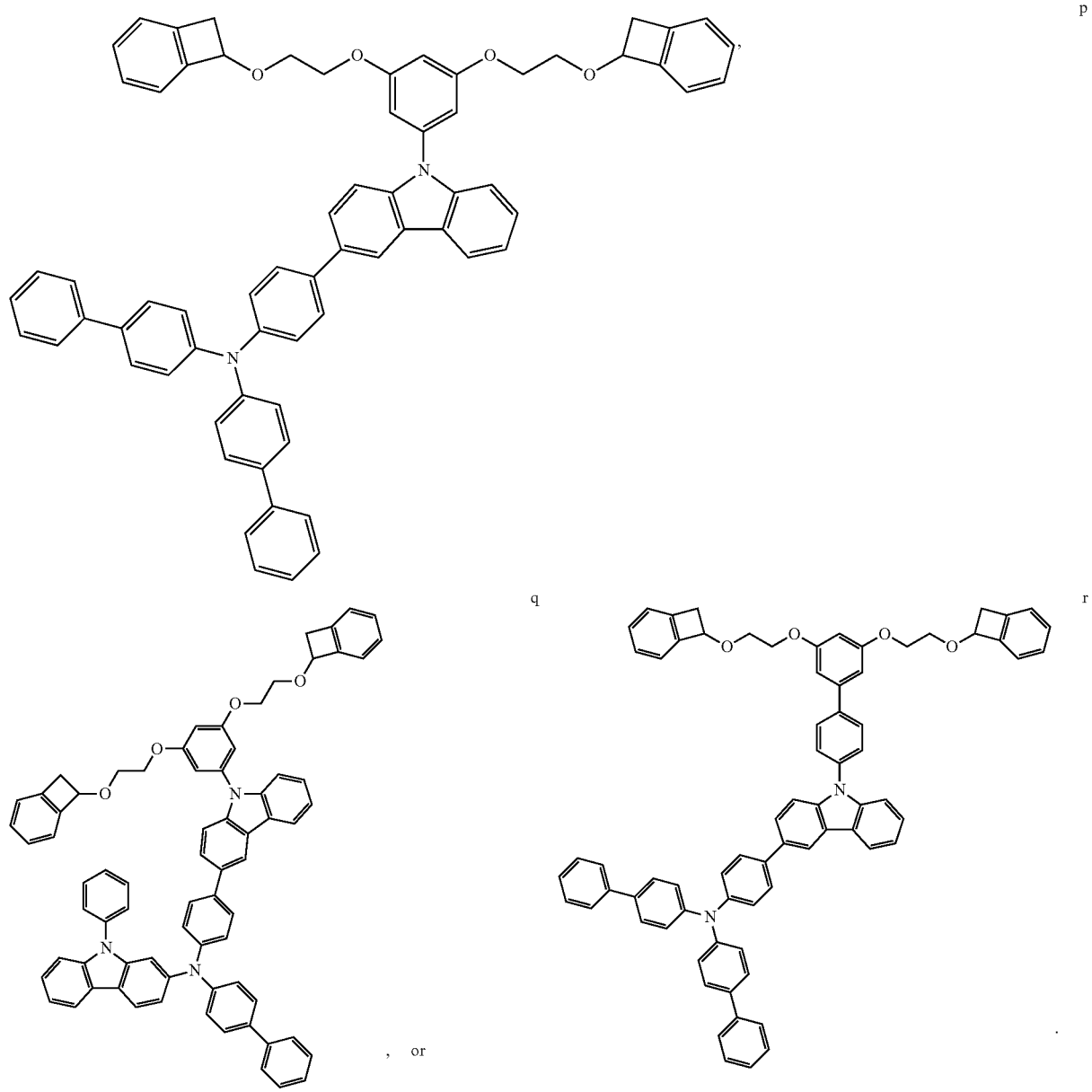
12. The composition of claim 1, wherein the Structure A has a molecular weight from 500 g/mole to 5000 g/mole.
13. The composition of claim 1, wherein Structure A has a triplet energy from 2.30 eV to 3.20 eV.
14. A film comprising at least one Layer A formed from the composition of claim 1.
15. An electroluminescent device comprising at least one component formed from the composition of claim 1.
* * * * *